(12) United States Patent
Stevenson et al.

(10) Patent No.: US 7,623,335 B2
(45) Date of Patent: Nov. 24, 2009

(54) HERMETIC FEEDTHROUGH TERMINAL ASSEMBLY WITH WIRE BOND PADS FOR HUMAN IMPLANT APPLICATIONS

(75) Inventors: Robert A. Stevenson, Canyon Country, CA (US); Richard L. Brendel, Carson City, NV (US); Christine A. Frysz, Marriottsville, MD (US); Haytham Hussein, Woodstock, MD (US); Scott Knappen, Annapolis, MD (US); Ryan A. Stevenson, Santa Clarita, CA (US)

(73) Assignee: Greatbatch-Sierra, Inc, Clarence, NY (US)

( * ) Notice: Subject to any disclaimer, the term of this patent is extended or adjusted under 35 U.S.C. 154(b) by 678 days.

(21) Appl. No.: 11/308,662

(22) Filed: Apr. 19, 2006

(65) Prior Publication Data

US 2006/0259093 A1 Nov. 16, 2006

Related U.S. Application Data

(60) Continuation-in-part of application No. 11/182,289, filed on Jul. 14, 2005, now Pat. No. 7,310,216, which is a division of application No. 10/842,967, filed on May 10, 2004, now Pat. No. 7,038,900, which is a continuation-in-part of application No. 10/825,900, filed on Apr. 15, 2004, now Pat. No. 6,999,818, and a continuation-in-part of application No. 10/377,272, filed on Feb. 27, 2003, now Pat. No. 6,765,780, and a continuation-in-part of application No. 10/377,086, filed on Feb. 27, 2003, now Pat. No. 6,765,779, and a continuation-in-part of application No. 10/377,018, filed on Feb. 27, 2003, now Pat. No. 6,888,715.

(60) Provisional application No. 60/548,770, filed on Feb. 27, 2004, provisional application No. 60/508,426, filed on Oct. 2, 2003.

(51) Int. Cl.
   *H01G 4/35* (2006.01)
(52) U.S. Cl. ............... 361/302; 361/306.1; 361/303; 361/305; 361/301.2; 333/182; 333/183; 333/185
(58) Field of Classification Search ............... 361/302, 361/303–305, 301.2, 301.4, 307, 306.3, 321.2; 333/182–185; 607/36, 37, 5, 7
   See application file for complete search history.

(56) References Cited

U.S. PATENT DOCUMENTS

| | | | |
|---|---|---|---|
| 2,756,375 | A | 7/1956 | Peck |
| 3,235,939 | A | 2/1966 | Rodriguez et al. |
| 3,538,464 | A | 11/1970 | Walsh |
| 3,920,888 | A | 11/1975 | Barr |
| 4,083,022 | A | 4/1978 | Nijman |
| 4,144,509 | A | 3/1979 | Boutros |
| 4,148,003 | A | 4/1979 | Colburn et al. |
| 4,152,540 | A | 5/1979 | Duncan et al. |
| 4,220,813 | A | 9/1980 | Kyle |
| 4,247,881 | A | 1/1981 | Coleman |
| 4,314,213 | A | 2/1982 | Wakino |
| 4,352,951 | A | 10/1982 | Kyle |
| 4,362,792 | A | 12/1982 | Bowsky et al. |
| 4,424,551 | A | 1/1984 | Stevenson et al. |

(Continued)

*Primary Examiner*—Nguyen T Ha
(74) *Attorney, Agent, or Firm*—Kelly Lowry & Kelley, LLC

(57) ABSTRACT

A feedthrough terminal assembly for active implantable medical devices includes a structural wire bond pad for a convenient attachment of wires from either the circuitry inside the implantable medical device or wires external to the device. Direct attachment of wire bond pads to terminal pins enables thermal or ultrasonic bonding of lead wires, while shielding the capacitor or other delicate components from the forces applied to the assembly during attachment of the wires.

58 Claims, 17 Drawing Sheets

U.S. PATENT DOCUMENTS

| | | |
|---|---|---|
| 4,456,786 A | 6/1984 | Kyle |
| 4,737,601 A | 4/1988 | Gartzke |
| 4,741,710 A | 5/1988 | Hogan et al. |
| 5,032,692 A | 7/1991 | DeVolder |
| 5,070,605 A | 12/1991 | Daglow et al. |
| 5,142,430 A | 8/1992 | Anthony |
| 5,333,095 A | 7/1994 | Stevenson et al. |
| 5,440,447 A | 8/1995 | Shipman et al. |
| 5,539,611 A | 7/1996 | Hegner et al. |
| 5,650,759 A | 7/1997 | Hittman et al. |
| 5,670,063 A | 9/1997 | Hegner et al. |
| 5,751,539 A | 5/1998 | Stevenson et al. |
| 5,759,197 A | 6/1998 | Sawchuk et al. |
| 5,825,608 A | 10/1998 | Duva et al. |
| 5,836,992 A | 11/1998 | Thompson et al. |
| 5,867,361 A | 2/1999 | Wolf et al. |
| 5,870,272 A | 2/1999 | Seifried et al. |
| 5,905,627 A | 5/1999 | Brendel et al. |
| 5,959,829 A | 9/1999 | Stevenson et al. |
| 5,973,906 A | 10/1999 | Stevenson et al. |
| 6,008,980 A | 12/1999 | Stevenson et al. |
| 6,031,710 A | 2/2000 | Wolf et al. |
| 6,414,835 B1 | 7/2002 | Wolf et al. |
| 6,459,935 B1 | 10/2002 | Piersma |
| 6,529,103 B1 * | 3/2003 | Brendel et al. ............... 333/182 |
| 6,545,854 B2 | 4/2003 | Trinh et al. |
| 6,566,978 B2 * | 5/2003 | Stevenson et al. ........... 333/182 |
| 6,619,763 B2 | 9/2003 | Trinh et al. |
| 6,765,780 B2 * | 7/2004 | Brendel et al. ............... 361/302 |
| 6,985,347 B2 | 1/2006 | Stevenson et al. |
| 6,987,660 B2 * | 1/2006 | Stevenson et al. ........... 361/302 |
| 6,999,818 B2 * | 2/2006 | Stevenson et al. ............. 607/37 |
| 7,035,077 B2 * | 4/2006 | Brendel ....................... 361/302 |
| 7,136,273 B2 * | 11/2006 | Stevenson et al. ........... 361/302 |
| 7,145,076 B2 * | 12/2006 | Knappen et al. ............ 174/50.6 |
| 2002/0166618 A1 | 11/2002 | Wolf et al. |

* cited by examiner

THERMOPLASTIC POLYIMIDE SUPPORTED
TAPE ADHESIVE

| ABLELOC (R) 5500 MECHANICAL PROPERTIES | TEST METHOD |
|---|---|
| 90° Peel Strength - 250 mil (6.3 mm) width<br>Alloy 42 substrate @ 25°C: 5.0 lb$_r$ (2.3 kg$_r$) peak<br>@ 230°C: 1.4 lb$_r$ (0.64 kg$_r$) peak<br><br>PI Coated Si Substrate @ 25°C: 5.5 lb$_r$ (2.5 kg$_r$) peak<br>@ 230°C: 1.2 lb$_r$ (0.55 kg$_r$) peak | MT-8 |
| Flatwise Tensile Strength - 250 mil$^2$ (6.3 mm$^2$)<br>Alloy 42 substrate @ 25°C: 3300 psi (93 kg)<br>@ 230°C: 450 psi (13 kg) | MT-1 |

(1) TH exposure - 16 hours, 85°C/85% RH

FIG. 5

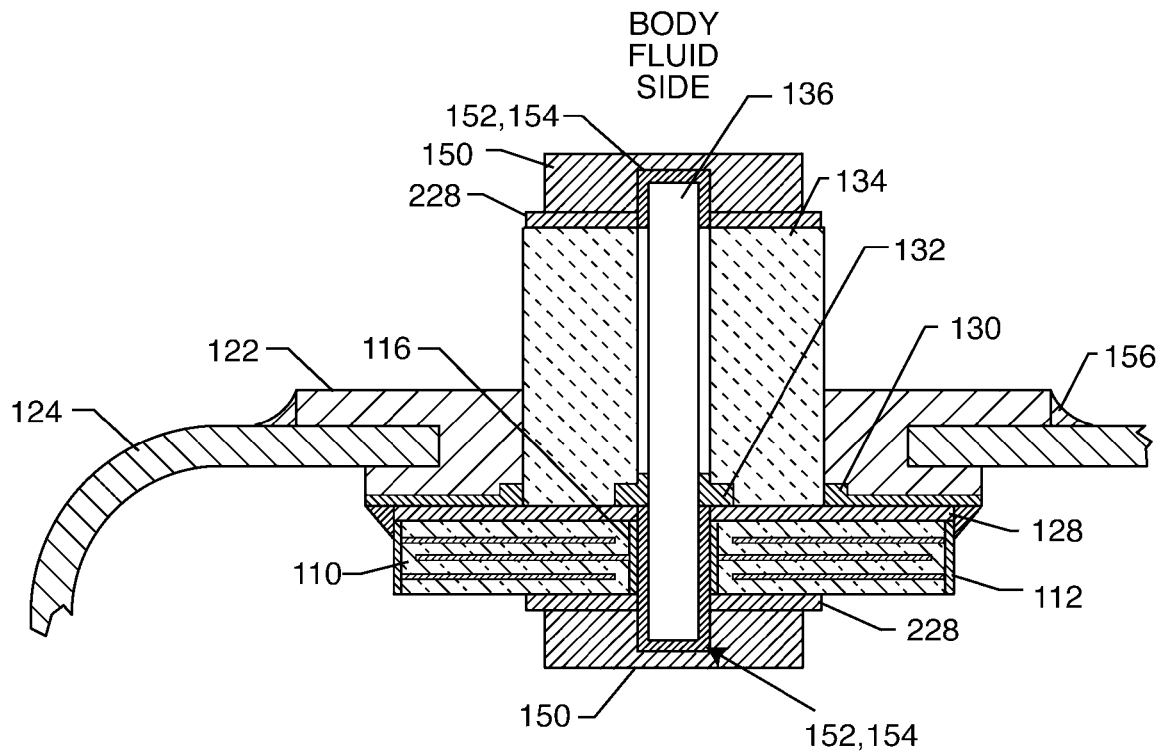
FIG. 6
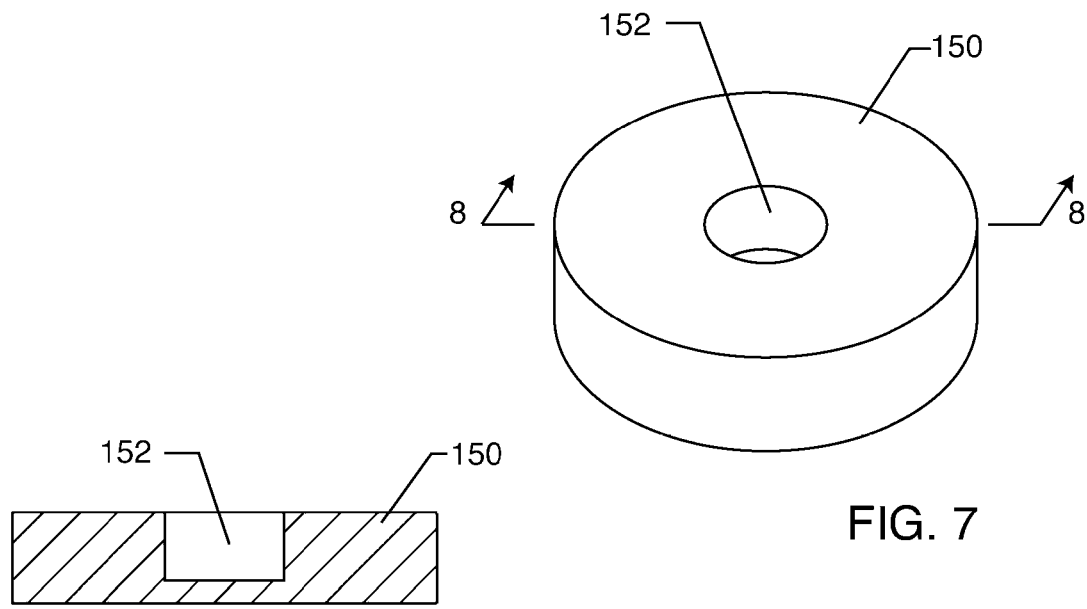
FIG. 8
FIG. 7

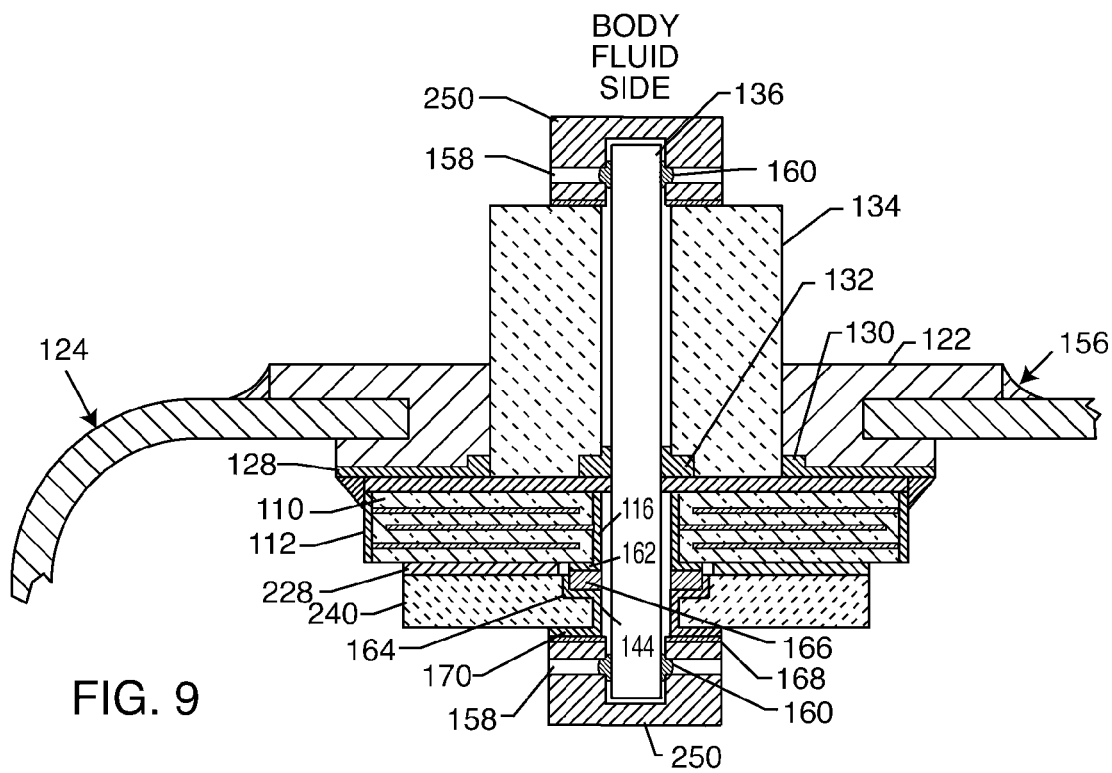
FIG. 9
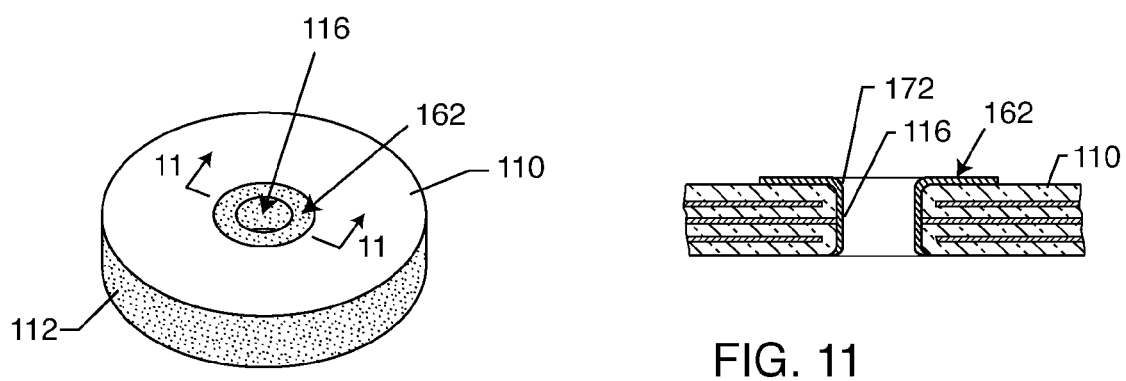
FIG. 10
FIG. 11
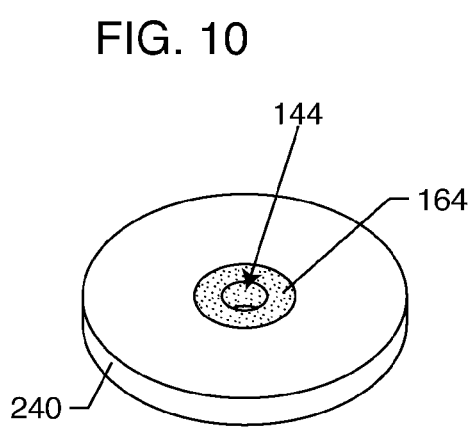
FIG. 12
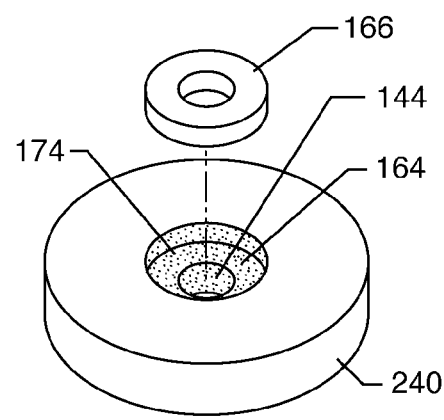
FIG. 13

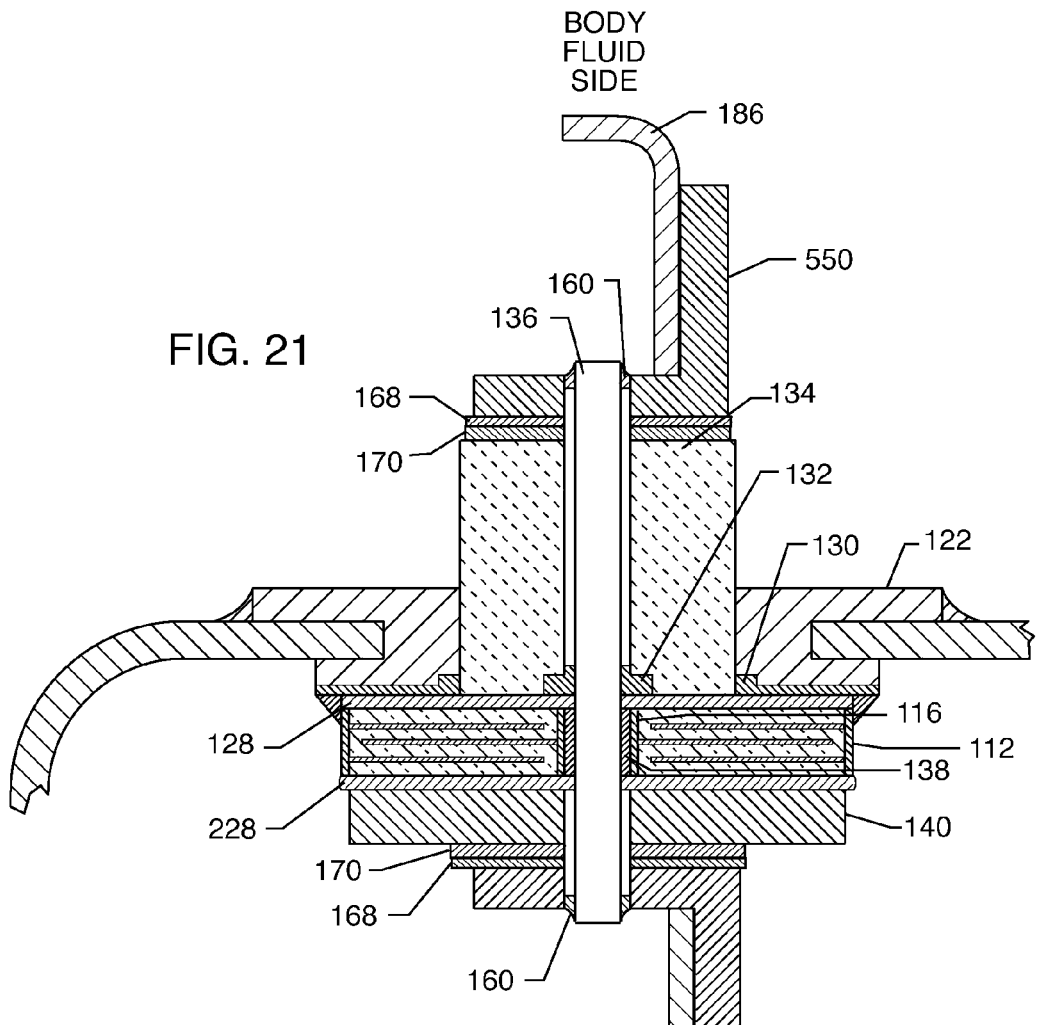
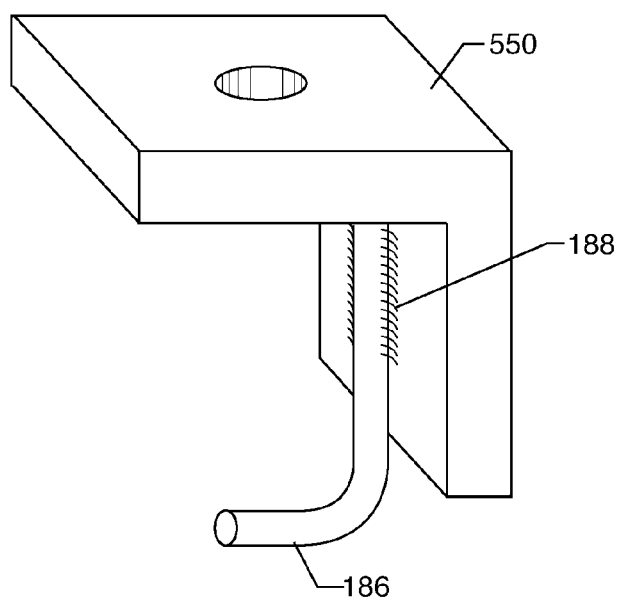
FIG. 21
FIG. 22

BODY
FLUID
SIDE

HERMETIC FEEDTHROUGH TERMINAL ASSEMBLY WITH WIRE BOND PADS FOR HUMAN IMPLANT APPLICATIONS

BACKGROUND OF THE INVENTION

This invention relates generally to hermetic feedthrough terminal subassemblies and related methods of construction, particularly of the type used in active implantable medical devices such as cardiac pacemakers, implantable defibrillators, cochlear implants, neurostimulators, active drug pumps, and the like, and those incorporating an electromagnetic interference (EMI) filter designed to decouple and shield undesirable EMI signals from an associated device. More particularly, the present invention relates to an improved hermetic terminal that includes bonding pads for convenient attachment of lead wires by way of thermal or ultrasonic bonding, soldering or the like. The bonding pads can be attached to the capacitor structure or to a terminal pin.

Feedthrough terminal assemblies are generally well known for connecting electrical signals through the housing or case of an electronic instrument. For example, in implantable medical devices, the terminal pin assembly comprises one or more conductive terminal pins supported by an insulator structure for feedthrough passage from the exterior to the interior of the medical device. Many different insulator structures and related mounting methods are known for use in medical devices wherein the insulator structure provides a hermetic seal to prevent entry of body fluids into the housing of the medical device. In a cardiac pacemaker, for example, the feedthrough terminal pins are typically connected to one or more lead wires within the case to conduct pacing pulses to cardiac tissue and/or detect or sense cardiac rhythms.

However, the lead wires can also undesirably act as an antenna and thus tend to collect stray electromagnetic interference (EMI) signals for transmission into the interior of the medical device. Studies conducted by the United States Food and Drug Administration, Mt. Sinai Medical Center and other researchers have demonstrated that stray EMI, such as RF signals produced by cellular telephones, can seriously disrupt the proper operation of the pacemaker. It has been well documented that pacemaker inhibition, asynchronous pacing and missed beats can occur. All of these situations can be dangerous or life threatening for a pacemaker-dependant patient. In prior devices, such as those shown in U.S. Pat. Nos. 5,333,095 and 4,424,551 (the contents of which are incorporated herein), the hermetic terminal pin subassembly has been combined in various ways with a ceramic feedthrough capacitor filter to decouple electromagnetic interference (EMI) signals to the equipotential housing of the medical device.

In general, the ceramic feedthrough capacitor which has one or more passages or feedthrough holes is connected to the hermetic terminal of the implantable medical device in a variety of ways. In order for the EMI filter feedthrough capacitor to properly operate, a low impedance and low resistance electrical connection must be made between the capacitor ground electrode plate stack and the ferrule, which, in turn, mechanically and electrically connects to the overall conductive housing of the implantable medical device. For example, in a cardiac pacemaker, the hermetic terminal assembly consists of a conductive ferrule generally made of titanium which is laser-welded to the overall titanium housing of the implantable medical device. This not only provides a hermetic seal but also makes the ferrule of the hermetic terminal a continuous part of the overall electromagnetic shield that protects the electronics of the implantable medical device from electromagnetic interference. The ceramic feedthrough capacitor is, in turn, electrically and mechanically bonded to the ferrule of said hermetic terminal. In the past, and, in particular, as described in U.S. Pat. Nos. 5,333,095 and 4,424,551, the connection is typically performed using a thermal setting conductive adhesive. One such material is a silver flake loaded conductive polyimide, silver flakes overlay each other, increasing their flake-to-flake contact area, and having a much lower inductance and lower resistance at high frequency.

FIG. 1 is a cut away perspective view of a prior art unipolar ceramic feedthrough capacitor 110. This capacitor 110 has a conventional external ground 112 formed by the conductive termination around its outside diameter. This is a conductive termination which would be electrically connected to the ferrule of the hermetic terminal of an implantable medical device. The inside diameter hole 114 is also metallized 116 for electrical connection to the lead wire that passes through the center passageway 114. One can see in the cut away the active 118 and ground 120 electrode plate sets. Feedthrough capacitor geometry is highly preferable for EMI filters in that it acts as a coaxial broadband transmission line filter. This means that a feedthrough capacitor offers effective attenuation over a very broad range of frequencies without the series resonance problem that plagues conventional rectangular monolithic ceramic chip capacitors.

FIG. 2 is the schematic diagram of the feedthrough capacitor of FIG. 1.

FIG. 3 is a cross-section drawing which illustrates the feedthrough capacitor 110 of FIG. 1 installed to the hermetically sealed ferrule 122 of a housing 124 of an implantable medical device in accordance with U.S. Pat. No. 5,333,095, entitled FEEDTHROUGH FILTERED CAPACITOR ASSEMBLY FOR HUMAN IMPLANT. This device is also referred to as a unipolar (one lead wire) EMI filtered hermetic terminal. It is also known as a one section single element EMI filter. The schematic diagram for the filter is shown in FIG. 4. It is possible to have multielement EMI filters (combinations of inductors and capacitors) with a single (unipolar) lead wire, or have multiple lead wires with a single element EMI filter (feedthrough capacitor only). The connection between the outside diameter metallization 112 of the feedthrough capacitor 110 and the ferrule 122 is accomplished with a thermal setting conductive adhesive 126. In the preferred embodiment, connection 126 is typically not a continuous connection 360 degrees around the entire outside diameter of the ceramic capacitor 110. The electrical connection material 126 is usually discontinuous to allow for helium leak detection and also to minimize thermal and mechanical stresses to the capacitor 110.

The capacitor 110 is surface mounted and bonded to the ferrule 122 of the hermetic terminal using an adhesive backed polyimide supported washer 128, which is further described in FIG. 6. The hermetic terminal of FIG. 3 is formed by gold brazes 130 and 132. Braze 130 makes a 360 degree mechanical and hermetic seal between the ferrule 122 and the alumina ceramic insulator 134. Gold braze 132 forms a 360 degree mechanical and hermetic seal between the lead wire or terminal terminal pin 136 and the alumina ceramic terminal 134. The capacitor ground electrode plates 120 are connected in parallel to the capacitor outside termination 112. The capacitor ground electrode plates 120, in turn, are connected to the ferrule 122 by way of the electrical connection material 126 disposed between the capacitor metallization 112 and the surface of the ferrule 122. In a typical medical implant EMI filter, the material 126 is of the group of solder, braze, or a thermal setting conductive polymer such as conductive polyimide or conductive epoxy. The electrical connection is made between the capacitor inside diameter metallization 116 and the terminal terminal pin 136 with connection material 138, which is typically of the same material described above with respect to connection material 126. If the terminal terminal pin 136 is of solderable material, which, for human implant applications, includes the group of platinum and platinum iridium biocompatible alloys, then material 138 can be solder, conductive thermal setting adhesives or the like. However, in the case where the terminal terminal pin 136 is of niobium, tantalum or titanium, solders and conductive adhesives generally cannot be applied directly to such pin materials. In this case, the terminal pin 136 would need pretreatment in order to eliminate contact problems associated with high resistance surface oxides.

The ceramic capacitor 110 is often comprised of relatively weak barium titanate, strontium titanate or equivalent high K dielectric. As a general rule, as one raises the dielectric constant, K, of a ceramic material, the structurally weaker it becomes. Leads extending from the circuitry of the implantable device to the feedthrough assembly, or those leads extending from the implantable device to the organ or another device, must be connected to the feedthrough terminal assembly. However, during ultrasonic or thermal wire bonding, considerable energy is imparted into the structure, which can damage the structure, and particularly the ceramic capacitor.

Moreover, for implantable medical devices, it is generally required that any of the electrical circuit connections that are in series with the input or output of the device should be of highly reliable connections. For example, in a cardiac pacemaker, the lead wires that are implanted in the heart sense both biologic electrical signals and also provide pacing pulses to correct cardiac arrhythmias. It is generally not acceptable to have an opening or break in this lead wire anywhere in the system that would then be reattached during initial manufacturing with solder, conductive thermal setting adhesives or the like.

SUMMARY OF THE INVENTION

Feedthrough terminal assemblies constructed in accordance with the present invention for use in active implantable medical devices generally comprise a conductive ferrule conductively coupled to a housing of the active implantable medical device. One or more conductive terminal pins extend through the ferrule in non-conductive relation. Typically, a non-conductive insulator is disposed between the terminal pin and the ferrule, and includes passageways therethrough for the one or more terminal pins. In accordance with the present invention, a lead wire bonding pad is conductively coupled to the terminal pin. In a particularly preferred embodiment, the bonding pad is attached to an end of the terminal pin on a body fluid side of the assembly. Accordingly, the bonding pad is comprised of, or coated with, a conductive and biocompatible material, such as a noble metal or stainless steel.

EMI filter terminal assemblies constructed in accordance with the present invention comprise, generally, at least one conductive terminal pin, a filter capacitor, which in the case of a feedthrough filter capacitor has a passageway through which one or more terminal pins extend, and one or more wire bond pads. An optional ferrite bead or ferrite bead inductor, as described in U.S. Patent Application Ser. No. 60/508,426, can also be included. The feedthrough capacitor is mounted to a hermetic seal subassembly in accordance with one or more prior art methods as described in U.S. Pat. Nos. 4,424,551, and 5,333,095. The feedthrough capacitor has first and second sets of electrode plates also known as the ground electrode plate set and the active electrode plate set. The terminal pin(s) extend through the passageway(s) of the capacitor in conductive relation with the active set of electrode plates. In a typical implantable electronic device application like a cardiac pacemaker, there is a hermetic insulator supported by a conductive substrate (usually a titanium ferrule) in which the terminal pin passes through in nonconductive relation. The capacitor may be bonded onto or into this insulator or separated from the insulator thereby forming a small air gap depending on the assembly method used. The outside diameter of the capacitor is generally installed in conductive relation with the conductive substrate or ferrule so that the feedthrough capacitor is properly grounded. An alternative arrangement is shown in U.S. Pat. No. 5,905,627, entitled INTERNALLY GROUNDED FEEDTHROUGH FILTER CAPACITOR.

In one embodiment, a substrate or circuit board having attached wire bond pads is co-bonded to the ceramic capacitor in such a way that they act as a monolithic structure. The co-bonded circuit board or substrate contains via holes, circuit traces and bonding pads or bonding areas such that it is convenient to attach wires from the circuitry inside the implantable medical device to the feedthrough capacitor structure via thermosonic bonding, ultrasonic bonding, thermal-setting conductive adhesives, soldering, welding, brazing, mechanical attachments or the like. In a preferred embodiment, a novel circuit board or substrate is co-bonded to the top surface of the ceramic feedthrough capacitor in accordance with the invention.

A novel aspect of the present invention is that both the ceramic feedthrough capacitor(s) and the circuit board or substrate can be made much thinner than conventional practice because they are co-bonded into a monolithic laminate structure. This co-bonded/laminated structure is analogous to a beam. By increasing the height of the beam one dramatically increases the moment of inertia of the beam. A beam with an increased moment of inertia is much more resistant to failure or cracking due to bending forces. For example, if there was a bending force which tended to deflect the composite structure in a downward fashion, the top of the capacitor would be in compression and the bottom would tend to be in tension. By raising the moment of inertia of this composite structure, the amount of deflection is minimized. Accordingly, a novel aspect of the present invention is that a circuit board or substrate can be added without greatly increasing the overall volume (height) of the EMI filter.

It is desirable that the circuit board or substrate be relatively thin. This means that materials having a high structural integrity must be used. The use of alumina, aluminum oxide, Fosterite, or polyimide as a substrate material is ideal.

In a preferred embodiment of the invention, it is desired to form one or more bond pads suitable for thermal or ultrasonic bonding. In such applications, a gold or gold plated bond pad is desirable. In the preferred embodiment, the bond pad is plated of ultrapure soft gold, such as 99.99% purity. Such gold is also known as yellow gold, is quite soft and to which forming a wire bond is easy. In a typical application, the wire bond pad is laid down directly on the substrate or it can be a Kovar or Alloy 42 attached metal pad with a nickel underplate and then finished with a soft gold over-plate. Chemical or photo resist techniques, electroplating, electroless plating and the like can be used to prevent deposition of plating, such as the gold, in the wrong places. The bond pad itself is typically Kovar or Alloy 42 but can include many other metals, ceramics and other materials.

Kovar or other metal wire bond pads are preferably attached to the outside or perimeter of the capacitor or a bonded substrate. Another embodiment is to add Kovar wire bond pads surrounding the feedthrough terminal pins where a convenient and highly reliable laser weld can be made. Another inventive concept is the idea of using the ceramic capacitor itself to directly attach metallized wire bond pads such as gold plated Kovar pads for wire bonding.

It should be noted that if lead-attachment is made by soldering or the like, the Kovar or Alloy 42 pad is generally not required. However, during ultrasonic or thermal wire bonding, considerable energy is imparted into the structure. Accordingly, in this case, a Kovar pad is desired to dissipate energy away from the underlying ceramic substrate or feedthrough capacitor structure. When wire bonding using thermosonic or ultrasonic energy, it is desirable to also use an alumina substrate which is co-bonded to the ceramic capacitor. This alumina substrate, when it is co-bonded, distributes the wire bonding shock and vibration forces across the entire surface of the ceramic capacitor. In general, ceramic materials, and capacitor dielectrics in particular, are strong in compression but very weak in tension. The relatively strong cobonded alumina substrate helps protect the relatively weak barium titanate, strontium titanate or equivalent high K dielectric used in the ceramic capacitor from fracturing or forming micro-cracks during application of these wire bonding forces. As a general rule, as one raises the dielectric constant, K, of a ceramic material, the structurally weaker it becomes. A low K alumina or aluminum oxide substrate is generally much stronger than barium titanate or other high K ceramics and is able to withstand these wire bonding forces. In this way, tension, shear and impact forces do not build up or become excessive in the capacitor dielectric. Various substrates are well known in the art with wire bond pads and are typically used in combination with hybrid circuit electrical connections and the like.

For implantable medical devices, it is generally required that any of the electrical circuit connections that are in series with the input or output of the device should be of highly reliable connections. For example, in a cardiac pacemaker, the lead wires that are implanted in the heart sense both biologic electrical signals and also provide pacing pulses to correct cardiac arrhythmias. It is generally not acceptable to have an opening or break in this lead wire anywhere in the system that would then be reattached during initial manufacturing with solder, conductive thermal setting adhesives or the like. Accordingly, it is a desirable feature of the present invention to have a laser welded connection between a Kovar or Alloy 42 pad or other conductive wire bond and the hermetic terminal pin, and/or a gold, gold alloy or CuSil (copper-silver alloy) braze between the Kovar pads and the perimeter or outside diameter of the substrate or capacitor. The connection from the feedthrough capacitor wire bond pad is generally accomplished by ultrasonic or thermosonic bonding of a pure gold wire directly to the pure gold plating of the pad. Attachment of lead wire(s) to wire bond pads can also be accomplished by soldering, conductive polymers, welding, brazing or a variety of mechanical attachment methods including machine screws and the like. In a typical pacemaker application, this pure gold wire is approximately 0.005 inch in diameter and would terminate on a similar wire bond pad on the pacemaker hybrid circuit substrate or circuit board on which microprocessor wire bonding and other implantable medical device electronics are mounted. Automated wire bonding equipment is readily available and well known in the art.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 5 is a table specifying the properties of a thermal plastic polyimide supported tape adhesive.

FIG. 6 is a sectional view similar to FIG. 5, illustrating use of a wire bond pad bonded or laminated onto the top of the capacitor over a shortened lead wire;

FIG. 7 is an enlarged perspective view of the wire bond pad of FIG. 9;

FIG. 8 is a sectional view taken generally along the line 8-8 of FIG. 7;

FIG. 9 is a sectional view similar to FIG. 9 illustrating another embodiment of the invention;

FIG. 10 is an inverted perspective view of the feedthrough capacitor illustrated in FIG. 9;

FIG. 11 is an enlarged sectional view taken generally along the line 11-11 of FIGS. 9-10;

FIG. 12 shows the alumina substrate of FIG. 9;

FIG. 13 illustrates an alternative embodiment of the alumina substrate of FIG. 12, incorporating a circular boss into which a counterbore holds an electrical connection material;

FIG. 21 is a fragmented cross-sectional view similar to FIG. 5, illustrating the use of an L-shaped wire bond cap;

FIG. 22 is a perspective view of the attachment of a lead wire to the L-shaped wire bond pad of FIG. 21;

DETAILED DESCRIPTION OF THE PREFERRED EMBODIMENTS

Figure 1:
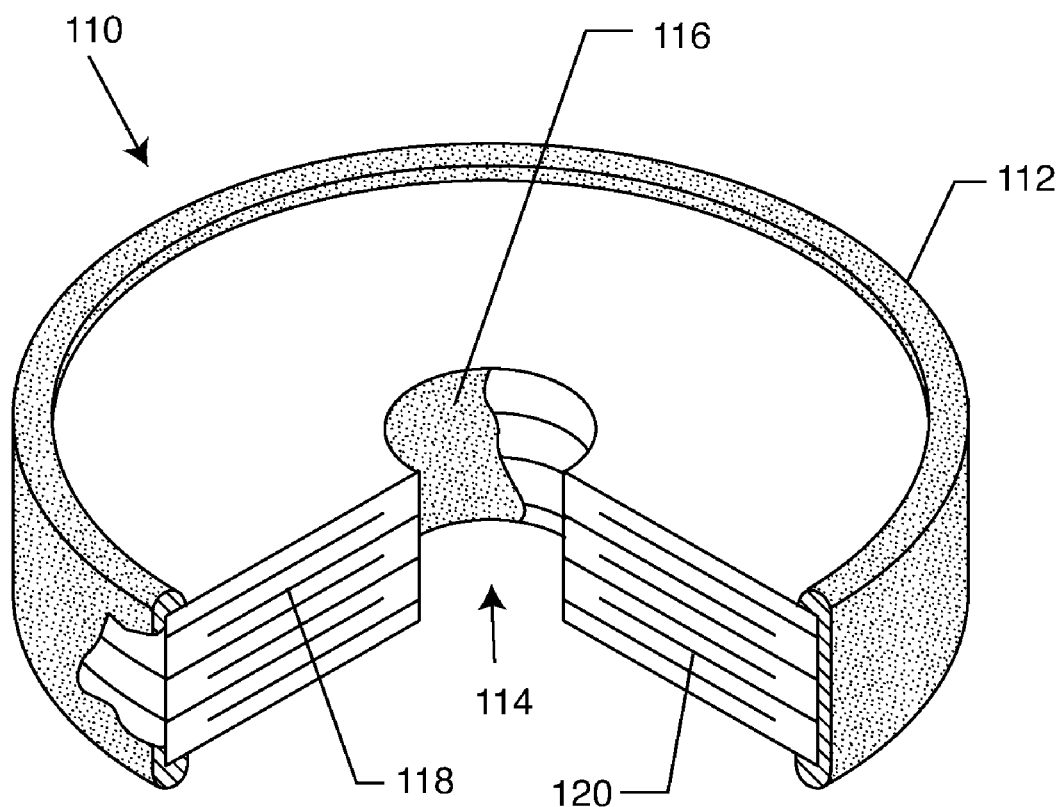
FIG. 1 is a cutaway perspective view of a prior art unipolar ceramic feedthrough capacitor.
Figure 2:
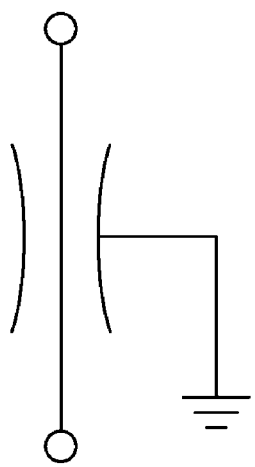
FIG. 2 is an electric schematic diagram of the prior art feedthrough capacitor of FIG. 1.

Reference will now be made in detail to presently preferred embodiments of the invention, examples of which are represented in the accompanying drawings for purposes of illustration. Such examples are provided by way of an explanation of the invention, not a limitation thereof. In fact, it will be apparent to those skilled in the art that various modifications and variations can be made in the present invention, without departing from the spirit and scope thereof. For instance, figures illustrated or described as part of one embodiment can be used on another embodiment to yield a still further embodiment. Still further, variations and selection of materials and/or characteristics may be practiced, to satisfy particular desired user criteria. Thus, it is intended that the present invention cover such modifications and variations as come within the scope of the present features and their equivalents. In the following description, functionally equivalent components of the various embodiments will be assigned the same reference number, or, if similarly related, a similar reference number increased by 100, for example, for sake of clarity and ease of explanation.

A novel method of providing a wire bond pad 150 is shown in FIG. 6. In this case, a counterbored Kovar or Alloy 42 disk, as also shown in FIGS. 7 and 8, is bonded or laminated 228 onto the top of capacitor 110 over a shortened lead wire or terminal terminal pin 136 by soldering, conductive thermal-setting adhesives, resistance welding, laser welding material 154 or the like.

FIG. 7 is an isometric view of the wire bond cap 150 and FIG. 8 is a cross-sectional view of the wire bond cap 150 of FIG. 6. In the preferred embodiment, such wire bond cap 150 as shown in FIGS. 6 and 7 would be constructed of Kovar or Alloy 42. The Kovar would be nickel plated and then over plated with soft gold suitable for compatibility with ultrasonic, thermal or thermal sonic wire bonding processes. Electrical connection material 154 is preferably placed in shear between the wire bond pad 150 and the terminal terminal pin 136. This is essential to form a highly reliable electrical connection that will withstand the vibration and shock forces associated with subsequent ultrasonic wire bond attachment(s). This shear area is accomplished by the counterbore area 152 shown in FIGS. 7 and 8. The wire bond cap 150 of FIG. 7 is also described in pending U.S. patent application Ser. Nos. 10/377,018, 10/377,272 and 10/377,086. FIGS. 44, 45, 46, 47A, 47B, 47C, 48 and 49 from pending U.S. patent application Ser. No. 10/377,086, entitled, EMI FEEDTHROUGH TERMINAL ASSEMBLY FOR HUMAN IMPLANT APPLICATIONS UTILIZING OXIDE RESISTANT BIOSTABLE CONDUCTIVE PADS FOR RELIABLE ELECTRICAL ATTACHMENTS, describes alternate methods to build the wire bond cap 150 shown in FIGS. 7 and 8.

In FIG. 6, an alternative method of forming the electrical connection 154 between the counterbore 152 of wire bond cap 150 and terminal terminal pin 136 is by prior art resistance welding techniques. In resistance welding, the counterbore 152 of wire bond cap 150 would fit very tightly onto terminal pin 136. Electrical contacts would be placed on the outside diameter of wire bond cap 150 and a current pulse from the resistance weld machine would be applied sufficient to cause heating and reflow of metals and/or the plating of wire bond cap 150 to form a low resistance metallurgical bond to terminal pin 136.

Referring now back to FIG. 6, as illustrated, electrical connection material 154 also makes a reliable and oxide free electrical connection to the gold braze area 132. This important feature is described by co-pending U.S. patent application Ser. No. 10/377,086. The gold braze material 132 penetrates through any surface oxidation on terminal pin 136, for example, if terminal pin 136 is niobium or tantalum, and thereby forms a highly conductive and reliable hermetic seal connection. In turn, electrical connection material 154 also makes an electrical connection to the inside diameter metallization 116 of feedthrough capacitor 110 and to the gold plated counterbore area 152 of the Kovar wire bond cap 150. This means that terminal pin 136 can be of any biocompatible material including oxidized materials such as niobium, and that no pretreatment, for example, sputter coating, is required to make a reliable electrical connection from terminal pin 136 to the feedthrough capacitor inside diameter metallization 116 or to the gold plated wire bond cap 150. In other words, no direct electrical contact from the capacitor inside termination 116 or the wire bond cap 150 is required to terminal pin 136.

FIG. 6 is a Table which specifies the properties of a thermal plastic polyimide supported tape adhesive 228 which is ideal for laminating the bond pad 150 of the present invention to the ceramic capacitor 110 or insulator 134 surface. The industry designation for this is ABLELOC®5500. This is the same polyimide supported tape adhesive 128 that is generally used to bond the ceramic capacitor 110 to the surface of the hermetic terminal 122. This material is convenient in that it can be die cut, stamped or laser cut into convenient geometries to co-bond a bonding pad 150 or an induction, or an alumina substrate 140 to the capacitor 110 or bond the capacitor to a hermetic terminal 122. In addition, polyimide is an ideal high-temperature material that will readily withstand the installation stresses into the implantable medical device caused by laser welding. A number of other bonding materials can also be used including adhesives, epoxies, glasses and the like.

In a particularly preferred embodiment of the present invention, a wire bond pad 150 is also connected to the end of the terminal terminal pin 136 on the body fluid side, as illustrated in FIG. 6. A connection of the wire bond pad 150 to the terminal terminal pin 136 and the illumine insulator 134 can be made in the same manner, as described above.

It should be pointed out that in human implant applications, the purpose of the hermetic terminal is to allow conductive terminal pins 136 to pass in nonconductive relationship through the titanium housing or can 124 of the pacemaker or implantable cardioverter defibrillator. Accordingly, all materials used on the body fluid side of such can or housing must be biocompatible. This limits the materials that can be used to noble metals, titanium, stainless steel and the like. Usually the terminal terminal pin 136 would be of platinum, platinum-iridium alloy, tantalum, niobium or the like. If the terminal pin 136 is platinum or platinum-iridium, these are highly solderable materials and therefore, it is easy to form a well wetted solder joint or conductive polymer connection between the bond pad 150 and the outside diameter of the terminal terminal pin 136. However, if the terminal pin is constructed of tantalum or niobium, these materials are generally not easily wetted by solder or conductive polymers. This can complicate the solder or conductive polymer joint. This is because niobium and tantalum form a heavy oxide layer on their surfaces. Accordingly, a niobium or tantalum terminal pin 136 must be pretreated so that a solder joint or connection with a conductive thermal setting material can be accomplished. It is a feature of the present invention to pretreat such leads such that they can be reliably electrically connected to bond pad 150. U.S. Pat. No. 6,159,560 describes a method of depositing silver on a tantalum pin to displace surface oxide and deposit a conductive finish suitable for making an electrical connection. There are other pin metal coating methodologies, including sputter or vacuum deposition (as described in U.S. Pat. No. 5,531,003), of materials such as gold, titanium and other conductors which can then be followed up with surface plating with gold, iridium or the like. Of course, instead of forming a solder or conductive polymer joint, the wire bond pad 150 could be resistance welded to the tip of the terminal terminal pin 136 as described above.

FIG. 9 illustrates another embodiment of the present invention. As previously mentioned, it is highly desirable in the output and input circuitry of implantable medical devices, that all electrical connections that are in series with the input and output be of highly reliable metallurgical joints. In other words, it is generally unacceptable to have a conductive thermal setting polymer, conductive polyimide, or less reliable metallurgical joint such as solder to rely on in series with the lead wires that are connected, for example, to the human heart. Mechanically robust and reliable metallurgical joints are preferred and are generally of the group of laser welding, brazing and the like. A preferred embodiment illustrated in FIG. 9, overcomes such deficiencies with a wire bond pad 250 that has been modified to accommodate laser beam welding. Another advantage of using this laser weld approach is that lower cost hermetically sealed feedthrough terminals can be used. Lower cost means that the terminal pins can be of niobium or tantalum construction instead of relatively expensive platinum or platinum-iridium alloys. Niobium and tantalum are notorious for forming heavy oxides on their surface and generally do not readily accept solder or thermal setting conductive adhesives. Previous methods of making the electrical contact with niobium or tantalum lead wires include an expensive process of pre-treating the niobium with vacuum or sputter deposition processes or other metallic overcoating. Such overcoat materials can be platinum, gold and the like.

Figure 3:
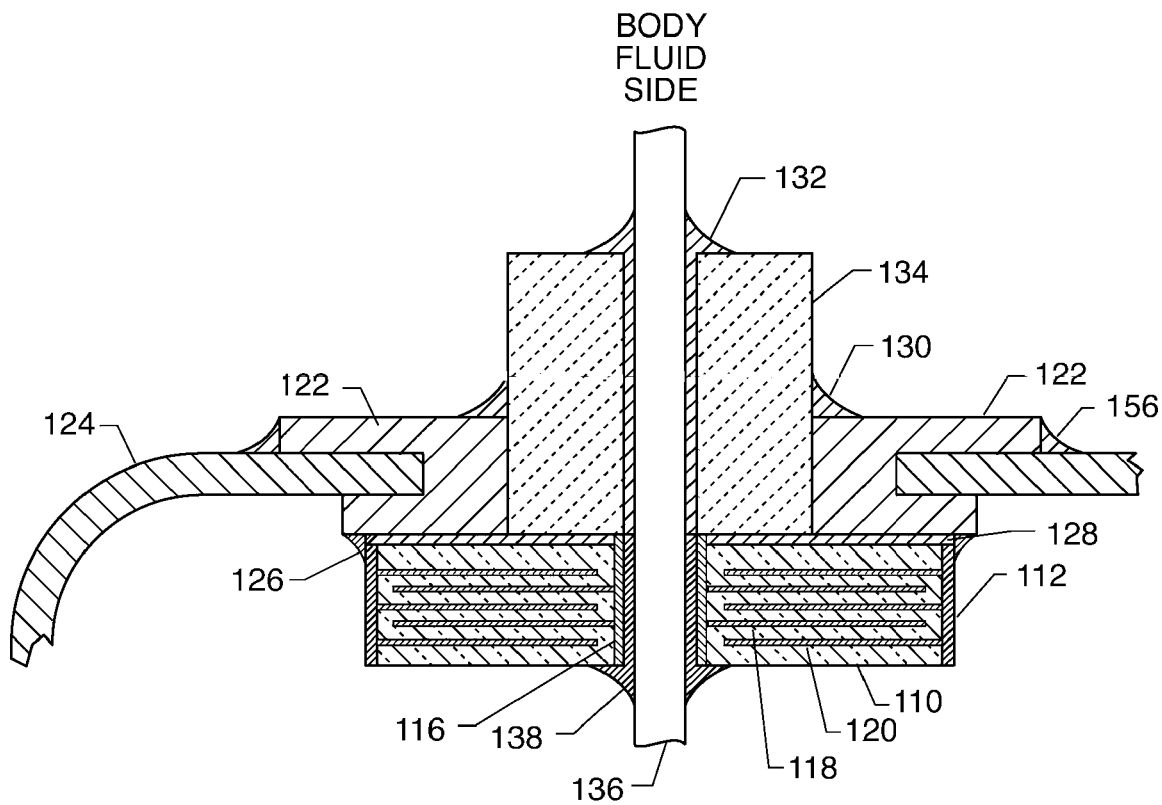
FIG. 3 is a fragmented cross-sectional view of the prior art feedthrough capacitor of FIG. 1 installed to a hermetically sealed ferrule.
Figure 4:
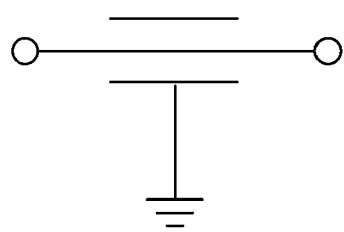
FIG. 4 is an electric schematic diagram for the prior art filter shown in FIG. 3.

FIG. 9 overcomes all of these previous deficiencies with the novel assembly method as illustrated. FIG. 9 is similar to the unipolar hermetic terminal assembly of FIG. 3 with a metallic ferrule 122. Co-bonded to this assembly is a prior art ceramic feedthrough capacitor 110. The ferrule 122 is designed to be laser welded 156 into the housing 124 of an implantable medical device such as a cardiac pacemaker or implantable cardioverter defibrillator (ICD). Gold braze 130 forms a hermetic seal connection between the ferrule 122 and the alumina insulator 134. The gold braze material 132 makes the hermetic connection between the terminal terminal pin 136 and the hermetic alumina insulator 134. It will be obvious to one skilled in the art that the alumina insulator 134 could be replaced by a variety of glasses or other sealing materials. The mounting of the unipolar capacitor 110 to this terminal is in accordance with prior art U.S. Pat. No. 5,333,095 and others. In FIG. 9, one can see that the alumina substrate 240 of the present invention is placed on top and co-bonded 228 to the ceramic capacitor 110. A counterbored wire bond cap 250 is placed over the top of the co-bonded alumina substrate 240 as shown. It is a novel aspect of the Kovar cap that it have one or more side through holes 158. These holes 158 are designed so that a laser beam from a laser welder can be directed into the through hole 158 to impinge its energy upon the terminal pin 136. Accordingly, a highly reliable laser weld connection 160 is formed between the counterbored wire bond cap 250 and the terminal terminal pin 136. On the body fluid side of the implantable device 124, preferably another wire bond pad 250 with the same arrangement as described above is laser welded 160 to the terminal terminal pin 136 extending out from the housing 124 of the implantable device and into the body fluid. This enables lead wires and the like to be attached directly to the wire bond pad 250, and extend to the organ in question, such as the heart, or other devices and the like.

Another novel aspect of the assembly shown in FIG. 9 is the fact that no electrical connection is needed from the inside diameter termination 116 of the feedthrough capacitor 110 and the terminal pin 136. This is because there is an electrical connection from a bottom termination surface 162 of the feedthrough capacitor 110 to a corresponding top termination surface 164 of the alumina substrate 240. The electrical connection material 166 joining these two surfaces can be solder, conductive thermal setting adhesives and the like. In turn, the wire bond cap 250 has been previously gold brazed 168 to a metallized surface 170 of the alumina substrate 240 as shown. As mentioned, the wire bond cap 250 is first gold brazed using a gold braze preform 168 to the metallization 170 that is on the surface of the alumina substrate 240. The laser weld 160 is then made by projecting a laser beam through the holes 158 in the wire bond cap 250.

This is better understood by examining FIGS. 10 through 13. FIG. 10 is an inverted isometric view of the feedthrough capacitor 110. One can see the typical inside diameter metallization 116. An important feature is the circular surface metallization band 162 which forms a continuous electrical connection with the inside diameter termination 116. In a preferred embodiment, the capacitor 110 would be tumbled either in the green or fired state prior to metallization application so that the sharp transmission corner from the passage hole to the surface is rounded. This makes for a more reliable electrical connection between the top circular metallization 162 and the inside diameter metallization 116. FIG. 11 is an enlarged cross-section taken along line 11-11 of FIG. 10, which illustrates the rounded corner 172. A sharp, nontumbled square corner could cause the metallization 116-162 to pull away during firing and becoming undesirably thin and discontinuous at the sharp edge. Such condition could lead to high resistance or even loss of circuit continuity.

Referring now to FIG. 12, one can see an alternative embodiment of the alumina substrate 240. In this embodiment, the alumina substrate 240 has an inside diameter or via hole metallization 144 which forms a continuous electrical connection with a similar circular metallization stripe 164. FIG. 13 illustrates an alternative embodiment of the alumina substrate 240 of FIG. 12 which incorporates a circular boss 174 into which a counterbore holds an electrical connection material 166. This boss also appears in FIG. 9. Electrical connection material 166 can be either a thermal setting conductive adhesive, solder a gold braze preform or the like. This gold brazed preform 166 is designed to seat against the metallized surface 164 of the alumina substrate 240. The wire bond cap 250 is pre-assembled by gold braze 168 to a circular metallized band 170 on the opposite side of the alumina substrate 240 as shown in FIGS. 9, 12 and 13. Referring now back to FIG. 9, one can see in the sandwiched construction that the capacitor circular metallization band 162 is electrically connected through material 166 to the corresponding metallization band 164 of the alumina substrate 240. After the wire bond cap 250 is gold brazed to the opposite side metallization surface 170 of the alumina substrate 240, there is then a continuous electrical connection from the inside diameter metallization of the feedthrough capacitor 116 through the inside diameter via hole metallization 144 of the substrate 240 all the way to its top metallization 170 and in turn, to the wire bond cap 250. The rest of the electrical circuit is completed by the laser weld connection between the wire bond cap 250 and the terminal terminal pin 136 shown as 160.

Another advantage is the ability to pre-assemble the wire bond cap 250 to the alumina substrate 240 to the feedthrough capacitor 110 and test and inventory this piece as a subassembly. The most expensive part of the hermetically sealed filtered terminal is the hermetic seal feedthrough 178 without a capacitor 110. This consists of the assembly of the terminal terminal pin 136 to the alumina insulator 134 to the ferrule 122 which is hermetically and mechanically connected by gold brazes 130 and 132. In this way, a large quantity of the hermetic terminal assemblies can be built and kept in inventory. A quantity of the pre-assemblies can also be built and kept in inventory. The capacitance value determined by the feedthrough capacitor 110 varies anywhere in human implant applications from 25 picofarads to around 9000 picofarads. In one cardiac pacemaker application alone, the capacitance value can vary from approximately 1000-9000 picofarads. Accordingly, it is an advantage to be able to inventory various capacitance values of the pre-assembly and keep them in inventory ready to be installed by co-bonding 128 and laser welding to the hermetic terminal and then final tested and shipped.

Figure 14:
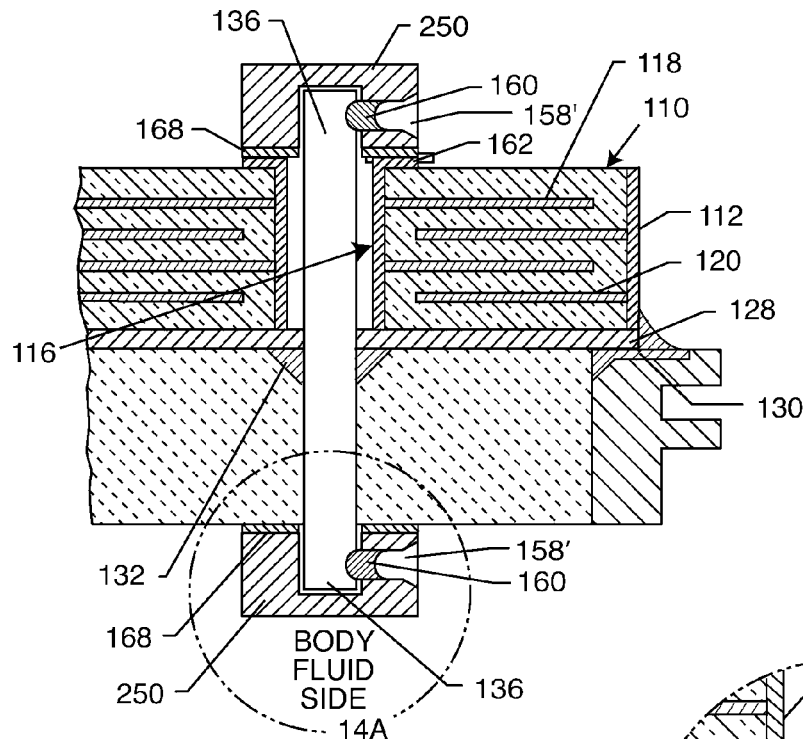
FIG. 14 is a partially fragmented sectional view similar to FIG. 12, illustrating use of an alternative wire bond pad.
Figure 14A:
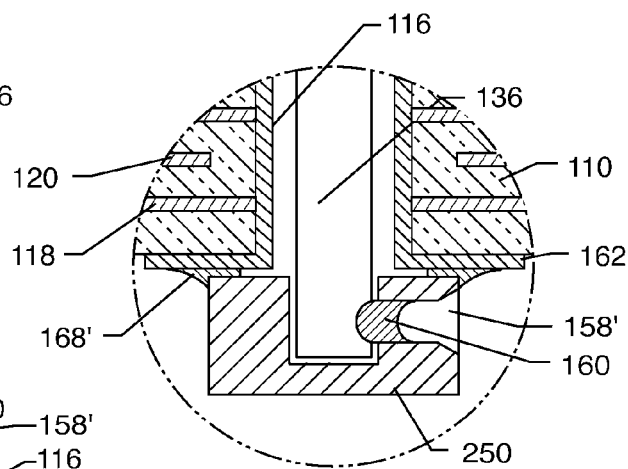
FIG. 14A is an enlarged, fragmented cross-sectional view of the area 14A of FIG. 14, illustrating an alternative configuration of components.

In the enlarged cross-sectional view FIG. 14A of FIG. 14, one can see that the wire bond pad 250 has had its laser through hole 158' enlarged at the opening point. This can be done by a counter sink, counterbore or the like. In this way, it is easier to direct the laser beam energy against terminal pin 136 thereby facilitating formation of the laser weld connection 160 between the wire bond cap 250 and the terminal terminal pin 136. This can be done on one or more sides around the circumference of the wire bond cap. As stated, the laser weld hole 158', shown in FIG. 14, has a counterbore which enlarges the opening for the laser beam. This enlarged opening also facilitates easier fixturing and robot programming to form the laser weld 160 between the wire bond cap 250 and the terminal terminal pin 136. In this particular embodiment, the terminal pin 136 can be of a non-wettable material such as niobium or tantalum. As one can see, there is an electrical connection material 168 which attaches the wire bond cap 250 directly to the capacitor top metallization 162. Capacitor top metallization 162 is continuous and also forms a termination surface 116 all around the inside diameter of the capacitor 110 feedthrough hole. The capacitor 110 depicted in FIG. 14 requires no additional electrical connection between the terminal terminal pin 136 and the feedthrough capacitor inside diameter termination 116. This is because there is continuous electrical connection from the capacitor active electrodes 118, to the capacitor inside diameter metallization 116 to the capacitor top circular termination 162 through electrical connection material 168 to the wire bond cap 250 and in turn by laser weld 160 to the terminal pin 136. This forms a highly reliable and low impedance electrical connection suitable for the EMI filtering purposes of the feedthrough capacitor 110. The electrical connection material 168 between the wire bond cap 250 and the capacitor circular metallization stripe 162 can be of solder, thermal setting conductive adhesives, brazes or the like. The assembly shown in FIG. 14 does not require an intermediate substrate 240 as described in previous FIGURES. FIG. 14 also illustrates a wire bond pad 250 having a similar enlarged opening 158' so as to permit a weld connection 160 with the terminal terminal pin 136 on the body fluid side of the assembly. In this embodiment, the wire bonding pad 250 is directly attached to the alumina insulator 134, which connection can be made in a variety of ways, including connection material 168, an adhesive-backed washer, polyimide or other non-conductive adhesive or the like.

FIG. 14A illustrates an alternative method of attaching the wire bond cap 250 to the top metallization 162 of the ceramic capacitor 110. Referring back to FIG. 14, wire bond cap 250 is attached to the top capacitor metallization 162 through a sandwiched electrical connection consisting of either gold braze, solder, conductive thermosetting adhesives or the like. Referring now to FIG. 14A, the electrical connection material has been relocated as shown. In this case, 168' would typically not be a gold braze but of the group of solder, conductive polyimide or conductive epoxy.

Figure 15:
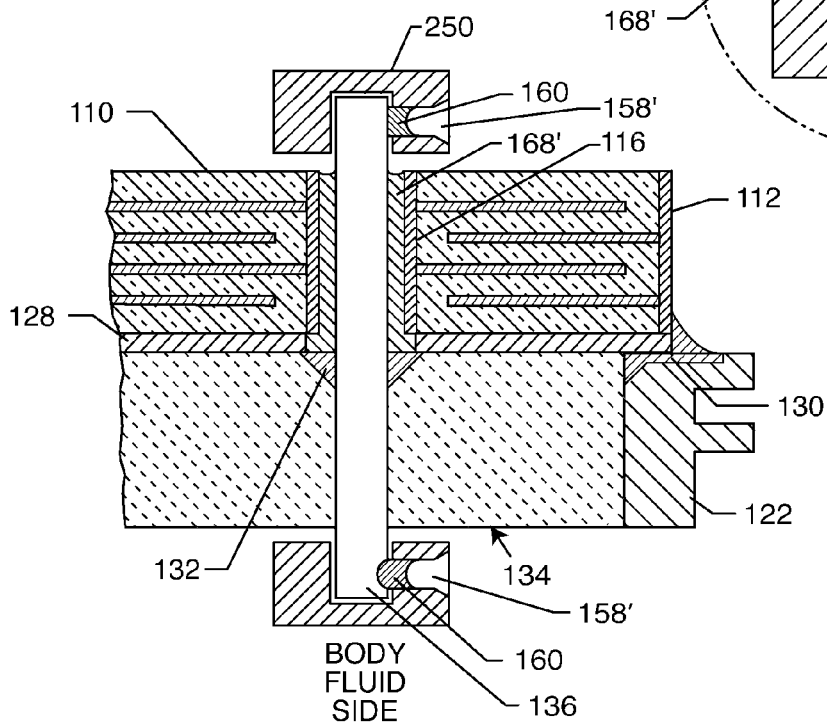
FIG. 15 is a view similar to FIG. 14, illustrating an alternative embodiment of the wire bond cap.

FIG. 15 illustrates an alternative embodiment of the wire bond cap 250 of FIG. 14. A laser weld joint 160 is formed in the same manner as previously described for FIG. 14. However, in this case, there is no top metallization 162 as a circular stripe on top of the capacitor 110. This has been removed along with the material 168 or 168' that formed an electrical connection between the wire bond cap 250 and the top metallization 162 of the FIG. 19 capacitor. In this embodiment, the electrical connection material 168' is only between the terminal pin 136 and the capacitor inside diameter metallization 116. An insulating material, such as a polyimide supported tape adhesive 128, has been placed between the capacitor 110 and the alumina of the hermetic seal 134 to prevent material 168' from leaking out underneath the capacitor 110 and shorting it out to the conductive ferrule 122. If the terminal pin 136 were of platinum iridium or pure platinum or similar highly solderable alloy, then no additional electrical connection is required. However, in the case where the terminal pin 136 is of a tantalum, niobium or other easily oxidizable material, then insulating material 128 would be pulled back away from the terminal pin 136, as shown, so that the electrical connection material 168' penetrates down and contacts to the gold braze 132 of the hermetic seal 134. This forms an oxide free electrical connection and is the subject of a pending U.S. patent application Ser. No. 10/377,086, the contents of which are incorporated herein.

Figure 16:
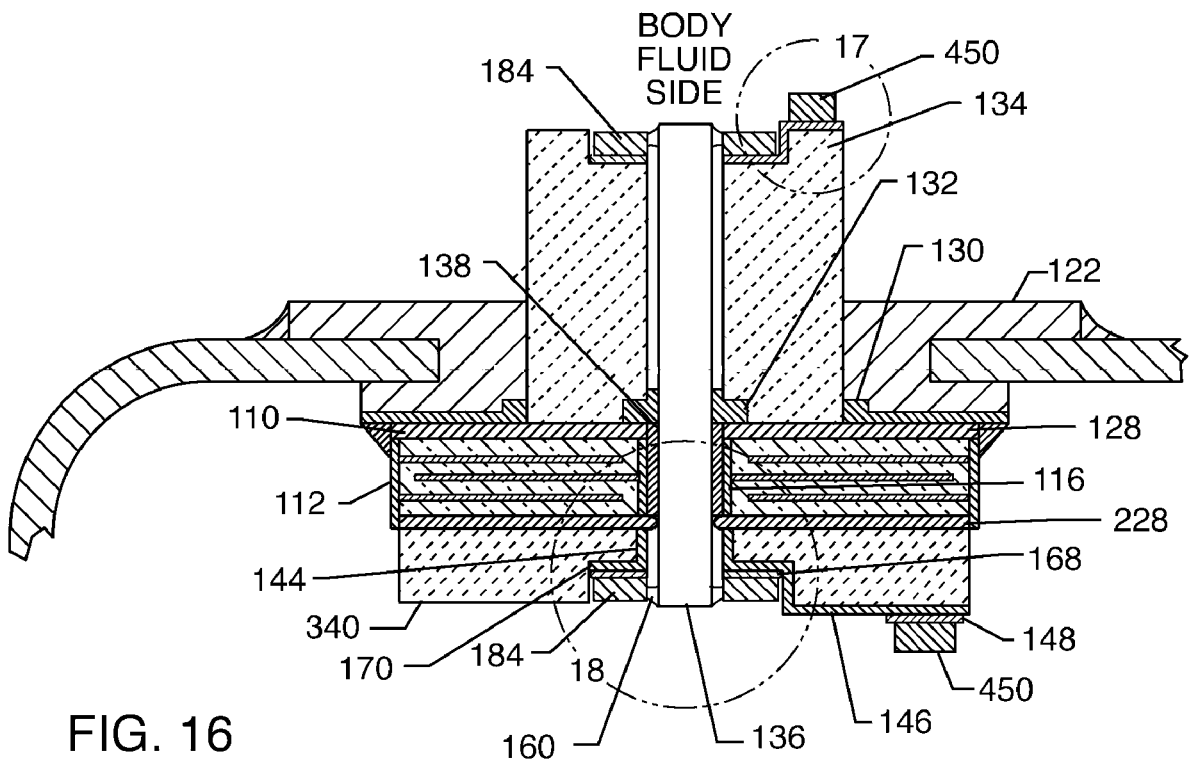
FIG. 16 is a fragmented cross-sectional view of the EMI filter hermetic terminal of FIG. 5 with modifications.
Figure 18:
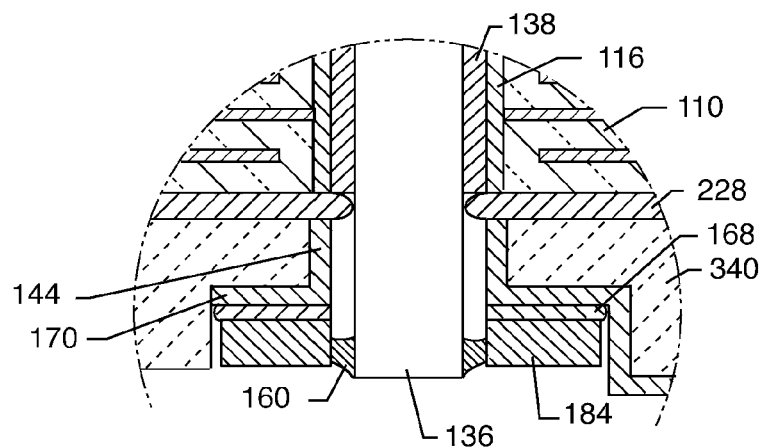
FIG. 18 is an enlarged, fragmented cross-sectional view of the area indicated by the number 18 in FIG. 16.

FIG. 16 is a cross-sectional view of the EMI filtered hermetic terminal of FIG. 9 modified with two improvements. As previously mentioned, it is highly desirable that all electrical connections that are in series with the input or output of an implantable medical device be of extremely high reliability. Accordingly, referring to FIG. 16, one can observe that there is a Kovar, Alloy 42 or equivalent metal insert ring 184 that is placed either on top of or into a counterbore of the alumina substrate 340. This is better understood by looking at the enlarged cross-section view of this same area of FIG. 16 in FIG. 18. According to FIG. 18, one can see the cross-section of the insert metal piece 184 which has been selectively plated with nickel and then pure gold. Ring 184 has been previously gold brazed to the metallization 170 of the alumina ceramic substrate 340 making a solid mechanical and electrical connection. The terminal terminal pin 136 is then attached by laser welding 160 to the metallic ring 184. Laser welding makes a very reliable and rugged electrical and mechanical joint in this important series connection.

Non-ceramic printed circuit board materials can also be used as a circuit board substitute for the ceramic substrate of the present invention and are mostly constructed from a resin reinforced by a fabric cloth. Epoxy (FR-4), polyimide and cyanate ester are the more common resin systems in use today. Fiberglass is the most popular fabric. It is important that the circuit board substrate be able to withstand the high temperatures caused by laser welding of the EMI filtered hermetic terminal assembly with wire bonds into the housing of an implantable medical device. Non-ceramic circuit board temperature range is most often expressed as the glass transition temperature (Tg) of the material. The material's Tg is the point above which the mechanical properties of the material begin to rapidly deteriorate. Printed circuit board materials change from hard, brittle substances to soft, rubber like substances after they reach their glass transition temperature. Typical Tg ratings for the more common material systems are as follows:

|  | Tg |
| --- | --- |
| Polyimides | 260° C.-270° C. |
| Modified Polymidies | 240° C.-260° C. |
| Cyanate Esters | 240° C.-250° C. |
| BT* Epoxies | 225° C.-240° C. |
| Composite Epoxies | 240° C.-260° C. |
| MultiFunctional EpoxieS | 160° C.-190° C. |
| TetraFunctional Epoxies | 140° C.-160° C. |
| Modified FR*-4' | 120° C.-130° C. |
| Standard FR*-4' | 115° C.-125° C. |

BT = Barium Titanate
FR = fiber reinforced

Accordingly, one can see from the above listing, that polyimides, followed by cyanate esters and BT epoxies would be a preferred choice after ceramic substrates as an alternative for the present invention. As used herein, the word substrate or alumina substrate can include any of the ceramic or non-ceramic materials listed above, in addition to many others that are not shown. It is desirable that the material that bonds the substrate of the circuit board to the ceramic capacitor be somewhat flexible and stress absorbing. This flexible layer will help prevent cracking of the ceramic capacitor due to any mismatches in the thermal coefficients of expansion. Accordingly, polyimide is an ideal material in that it forms a ring type of molecule after it goes through its glass transition temperature of approximately 260° C. Compared to epoxy, this material tends to absorb stresses and is quite resilient.

The construction of such substrates with circuit trace wire bond pads is well known in the art. Photo-resist, chemical etching, automated screen printing, silk screening, selective plating, screen printing and thin or thick film deposition methods are typically used to lay down the conductive circuit trace patterns, the bond pads or "lands" and the location and metallization of via holes.

Screen Printing Ink Formulations—The ink consists of four distinct groups of intermediates, which are thoroughly mixed and blended, yielding a homogeneous product:

| | |
| --- | --- |
| Functional Phase | Consists of metal powders (Pt, Pd, Ag, Au, etc.) in conductive inks, metals and/or metal oxides ($RuO_2$, $Bi_2 Ru_2O_7$, Pd, Ag) in resistors and ceramic/glass ($BaTiO_3$, glass) in dielectric temperature firing. |
| Binder Phase | To hold the ink to the ceramic substrate, and merges with the ceramic during high temperature firing. |
| Vehicle | Acts as the carrier for the powders and is composed of both volatile (solvents) and non-volatile (polymers) organics. These evaporate and burn off during the early stages of drying and firing, respectively. |
| Modifiers | Are small amounts of proprietary additives which control behavior of the inks before and after processing. |

1. Conductor Pastes—Single metal systems (such as, Pd, Ag, Au, Ni, etc.).
2. Conductor Pastes—Binary metal systems (such as, Ag/Pd, Ag/Pt, etc), Tungsten (W), Tungsten/Nickel and equivalent.
3. Conductor Pastes—Ternary metal systems (such as, 40 Au/40 Pd/20 Pt, 60 Ag/20 Pt/20 Pd, 35 Ag/25 Pd/20 Au/20 Pt, etc.).
4. High fire systems (such as, 30 Ag/70 Pd with $BaTiO_3$ or ZrO additives, 100 Pd, etc.).
5. Base metal systems (such as, Ni with $BaTiO_3$ or ZrO additives, etc.)

Substrate via holes are typically formed by automated pattern recognition drilling machines. There are a number of methods of providing metallization on the circuit paths, the bonding pads and through the via holes, including screen printing selective plating, metallization vacuum pull through, screen printing, cladding followed by selective etching, physical vapor deposition (PVD), chemical vapor deposition (CVD), and the like. Since these techniques are well known in the art, they will not be completely described herein.

Figure 17:
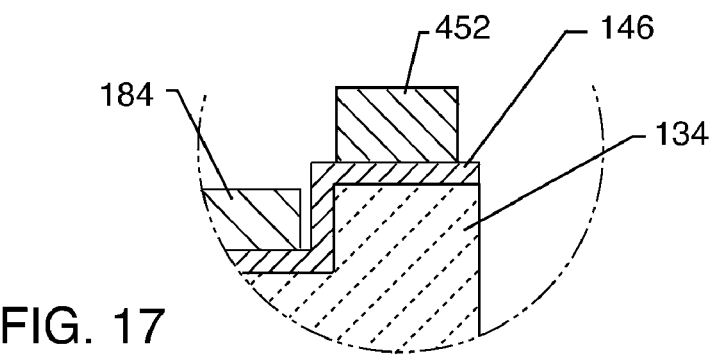
FIG. 17 is an enlarged sectional view of area "17" of FIG. 16, illustrating a bonding pad used in accordance with the present invention.
Figure 19:
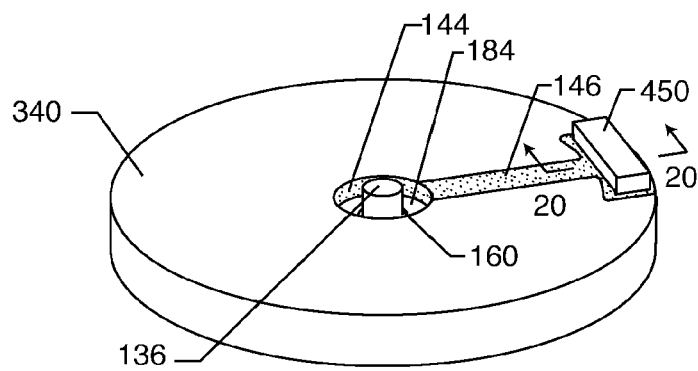
FIG. 19 is an inverted perspective view of the alumina substrate of FIG. 16.
Figure 20:
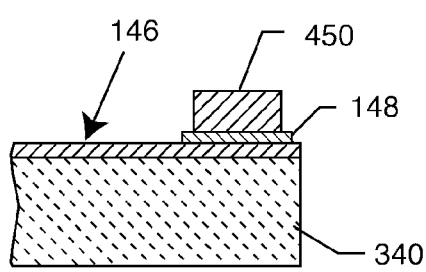
FIG. 20 is an enlarged, fragmented cross-sectional view taken along the line 20-20 of FIG. 19.

FIG. 20 is a cross-sectional view from FIG. 19 which better illustrates the mounting of the wire bond pad 450. As one can see, wire bond pad 450 has been electrically and mechanically attached to the circuit trace 146 using braze preform 148. This brazing operation would typically be performed on the alumina substrate 340 in a high temperature vacuum-brazing furnace. The braze joints 168 and 148 of FIG. 16, which attaches the ring 184 to the alumina substrate metallization 170 and the wire bond pad 450 to the alumina substrate 340 metallization 146 would typically be done prior to capacitor bonding at the same time in vacuum brazing furnace re-flow operation. FIG. 17 is an enlarged cross-sectional view from area "17" of FIG. 16, also illustrating the mounting of a wire bond pad 450 to the alumina insulator 134 using a circuit trace 146.

Referring again back to FIG. 16, one can see that the electrical connection material that electrically connects the inside diameter metallization 116 of the feedthrough capacitor 110 to the terminal terminal pin 136 also directly contacts the hermetic terminal gold braze material 132. Accordingly, it is an important feature of the novel EMI filtered terminal with wire bond substrate as shown in FIG. 16 that the terminal pin 136 can be of both solderable or heavily oxidized materials. Specifically, terminal terminal pin 136, as shown in FIG. 16, can be of the group of niobium, tantalum, titanium or other heavily oxidized materials. Normally, such heavily oxidized materials are not readily wettable with solder or suitable for attachment using a thermal setting conductive adhesive. However, as described in pending U.S. patent application Ser. No. 10/377,086, it is not necessary to make direct contact to the pin if contact is made to the gold braze material of the hermetic terminal 132. It is important to note that the manufacturing step of brazing gold material 132 to the terminal pin 136 burns through any such surface oxides or contamination and makes a very highly reliable hermetic and electrical connection to the terminal pin 136. In turn, direct contact of the thermal setting conductive adhesive or solder material 138 makes a highly reliable, low impedance, electrical connection for the proper operation of the feedthrough capacitor EMI filter 110.

Referring once again to FIG. 16, a similar electrical connection from the insert ring 184 to the terminal pin 136 is formed by the laser welding material 160. This laser weld also burns through any surface oxide on niobium, tantalum, or titanium pins and the like, thereby making a highly reliable electrical connection from the terminal pin 136 to the ring 184 which has been previously gold brazed to the surface metallization 170, of substrate 340.

In summary, the novel feedthrough capacitor with substrate as described in FIG. 16 has a number of advantages, including the obvious one of having highly reliable brazed electrical connections, and being suitable for wire bonding, but also suitable for use with literally any type of biocompatible terminal pin 136.

FIG. 21 illustrates a cross-sectional view of the present invention with an L-shaped wire bond cap 550. This wire bond pad 550 is typically Kovar or Alloy 42 and is gold plated. Also shown in FIG. 21 is the cross-section of a wire bonded lead wire 186. The attachment of lead wire 186 to the L-shaped wire bond pad 550 is better seen in isometric view FIG. 22. As one can see, lead wire 186, which is routed to internal implanted medical device circuitry, has been wire bonded in the area shown as 188 to the wire bond pad 550. It is typical in the art that lead wire 186 be a small diameter, pure gold or aluminum wire, such as a wire 0.005 inches in diameter. The wire bond connection 188 is typically formed by ultrasonic or thermosonic processes that are very well known in the art. On the body fluid side of the assembly, an L-shaped wire bond cap 550 is bonded to the alumina insulator 134, and has a conductive connection 160 to the terminal pin 136. A lead wire 186 is attached thereto, such as by ultrasonic or thermosonic processes, and extends to a location outside of the device, such as an organ within the body.

Figure 23:
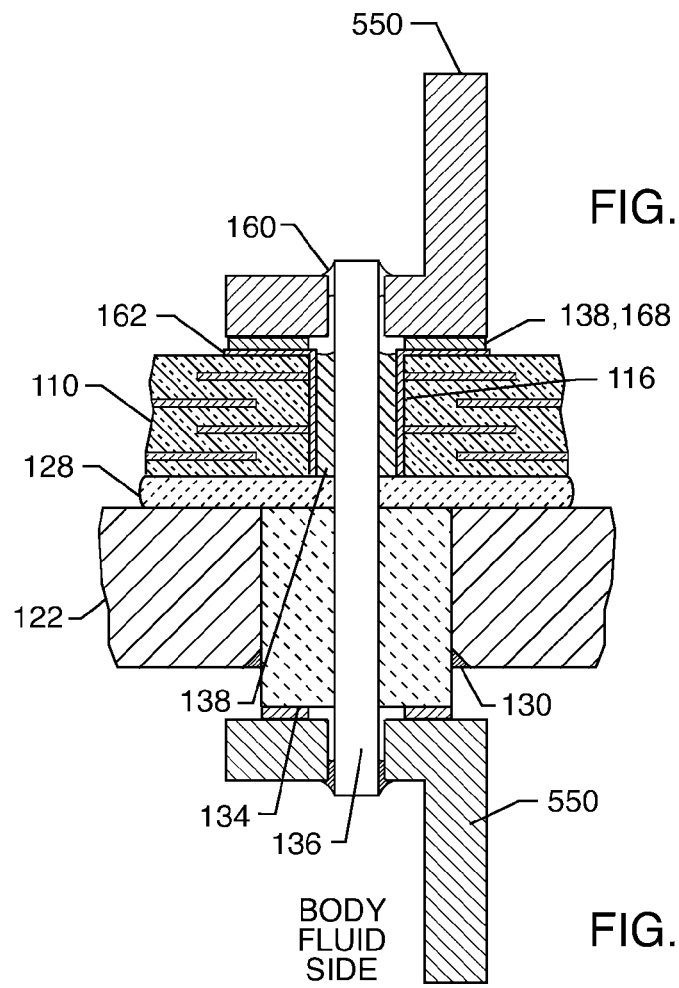
FIG. 23 is a sectional view of an alternative wire bond pad arrangement in comparison with that illustrated in FIG. 21.

FIG. 23 shows an alternative embodiment to that previously described in FIG. 21. In both cases, there is an L-shaped wire bond pad 550. The difference in FIG. 23 is that the wire bond pad 550 has been directly attached to the top of the ceramic feedthrough capacitor 110. In this case, there is not an alumina or other substrate 140 that is intermediary between the wire bond pad 550 and the top surface of the ceramic capacitor 110. The wire bond pad 550 is electrically and mechanically attached to the top of the ceramic capacitor using a conductive thermal setting polymer 138, a gold braze or a solder 168. A laser weld connection 160 is formed between lead wire 136 and the wire bond pad 550 as shown. The wire bond pad 550 on the body fluid side of the assembly is attached to the terminal pin 136 and the alumina insulator 134 in the same manner. FIG. 23 is a lower cost alternative, but is not considered to be as mechanically robust as having an alumina or equivalent material substrate 140 placed between the wire bond pad 550 and the ceramic capacitor 110. In FIG. 23, the ultrasonic wire bonding forces that would be applied during the attachment of the lead wire 186 (not shown) would put substantial mechanical stress onto the relatively fragile ceramic capacitor 110 itself. This must be a highly controlled process so that microfractures are not induced into the ceramic capacitor 110. Such microfractures have been shown to cause immediate or latent failure (electrical short circuit) of capacitor 110. Such short circuiting could be life threatening to a pacemaker patient.

Figure 24:
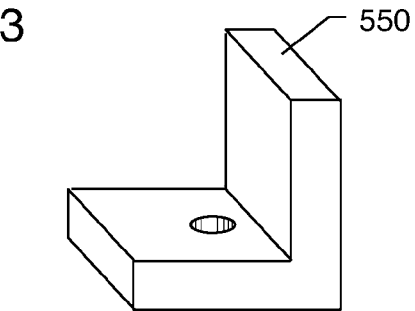
FIG. 24 is a perspective view of the L-shaped wire bond pad of FIGS. 23 and 21.
Figure 25:
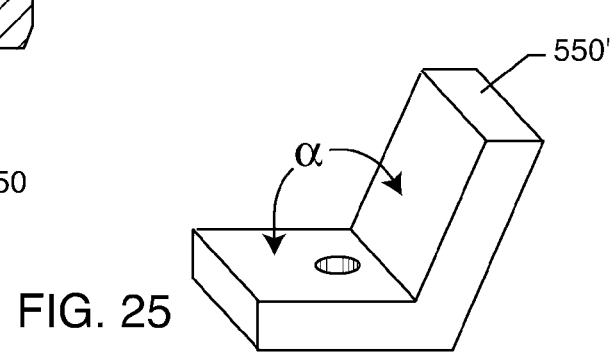
FIG. 25 is a perspective view similar to FIG. 24, illustrating the configuration of an alternative wire bond pad.

FIG. 24 is an isometric view of the L-shaped wire bond pad 550, previously described in FIG. 23. FIG. 25 is a similar wire bond pad 550' as described in FIG. 24, except that it is angled ($\propto$) to line up with the geometry or architecture of the internal circuits of the implanted medical device. As shown in FIG. 25, any convenient angle ($\propto$) can be used.

Figure 26:
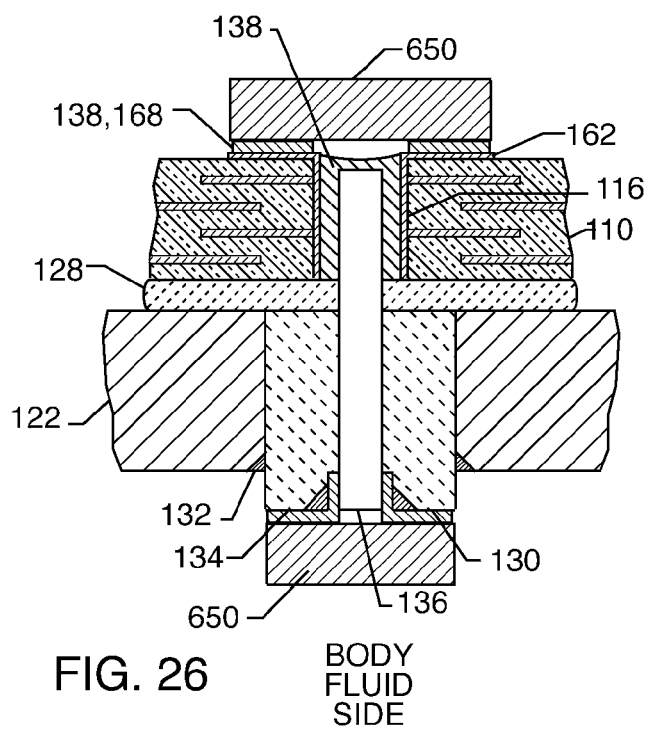
FIG. 26 is a sectional view similar to FIG. 23, illustrating the use of a circular or rectilinear wire bond pad.
Figure 27:
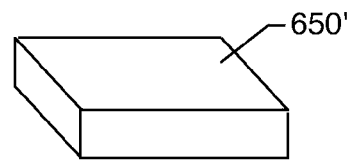
FIG. 27 is a perspective view of a rectilinear wire bond pad that could be incorporated into the assembly of FIG. 26.
Figure 28:
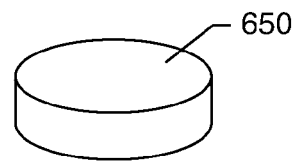
FIG. 28 is a perspective view of a circular wire bond pad that can be utilized in FIG. 26.

FIG. 26 is similar to FIG. 23 with a circular or rectilinear wire bond pad 650 or 650'. In FIG. 26, direct attachment is made from the wire bond pad 650 to the top surface metallization 162 of ceramic capacitor 110. The wire bond pad 650 on the body fluid side is attached to the terminal pin 136 with a conductive adhesive 130 or the like, which also bonds the wire bond pad 650 to the alumina insulator 134. As described in FIG. 23, there is no alumina or other substrate 140 that is intermediary between the wire bond pad 650 and the ceramic capacitor 110. Attachment of the circular wire bond pad 650 can typically be done by thermal setting conductive adhesive 138 or brazing or solder 168. Generally, a gold braze would not be used since braze materials tend to be too brittle and could induce microfractures into the ceramic capacitor.

Figure 29:
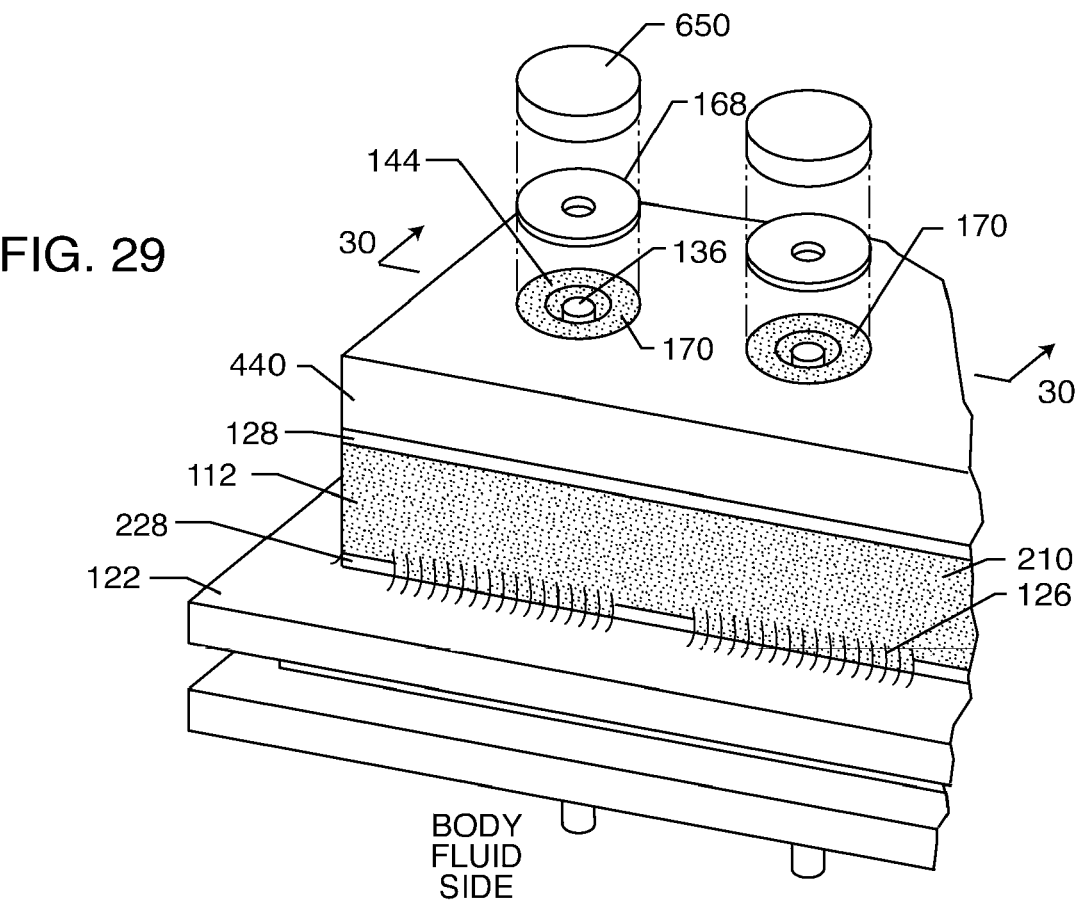
FIG. 29 is a fragmented perspective and partially exploded view of a bipolar feedthrough terminal assembly with wire bond caps.
Figure 30:
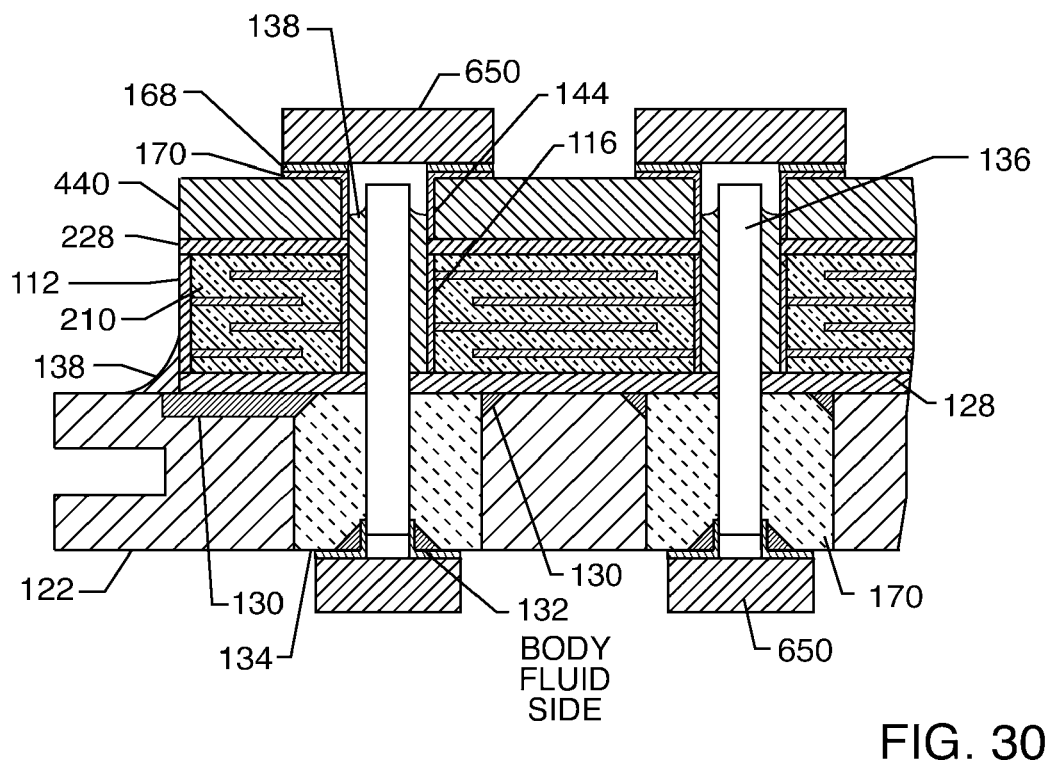
FIG. 30 is an enlarged, fragmented cross-sectional view taken generally along the line 30-30 of FIG. 29.

FIG. 29 illustrates the top view of a bipolar capacitor of the present invention. In this embodiment, exploded away circular wire bond pads 650 are placed over the top of the feedthrough holes of substrate 440 for convenient attachment of lead wires 186 (not shown). This is better understood by observing the cross-section of FIG. 29 illustrated in FIG. 30. As shown in FIG. 30, a circular wire bond pad 650 is attached to the top surface via metallization 170 of the ceramic substrate 440. The attachment of the circular wire bond pad 650 is by gold brazing 168 to the top metallization 170 of the alumina substrate 440. In this case, the terminal pin 136, which comes from the hermetic terminal consisting of 122, 130, 132, 136 and 134, is shortened as shown. The alumina substrate 440 is co-bonded using a nonconductive polyimide preform 228 to the top surface of the ceramic capacitor 210. The electrical connection material 138 is typically a conductive thermal setting polymer, such as a conductive polyimide, solder or the like. The electrical connection material 138 electrically connects the inside diameter or via hole metallization 144 of the substrate 440 to the terminal pin 136 and in turn to the inside diameter metallization 116 of the feedthrough capacitor 210. On the body fluid side of the assembly, as illustrated in FIG. 30, preferably wire bond pads 650 are conductively coupled to the terminal pins 136 via metallization 170 or the like. This enables the attachment to of lead wires (not shown) directly to these wire bonding pads 650 on the body fluid side of the device. Of course, it will be readily appreciated by those skilled in the art that such materials on the body fluid side, including the wire bonding pads 650, must be comprised of a biocompatible material, such as a noble metal, stainless steel, titanium or the like.

Figure 31:
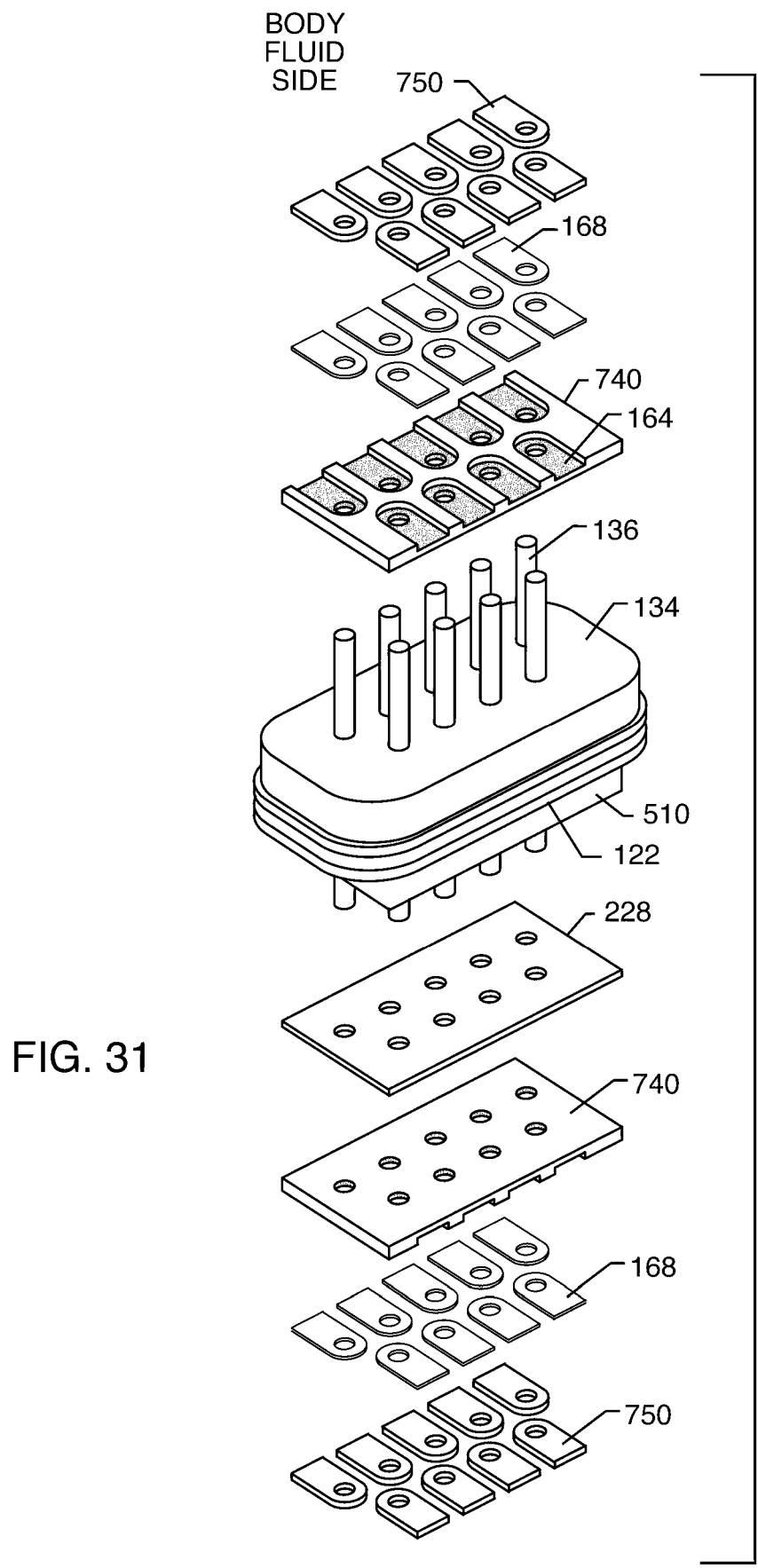
FIG. 31 is an exploded perspective view of an internally grounded dual inline 9-pole filter feedthrough capacitor hermetic terminal embodying the present invention.
Figure 32:
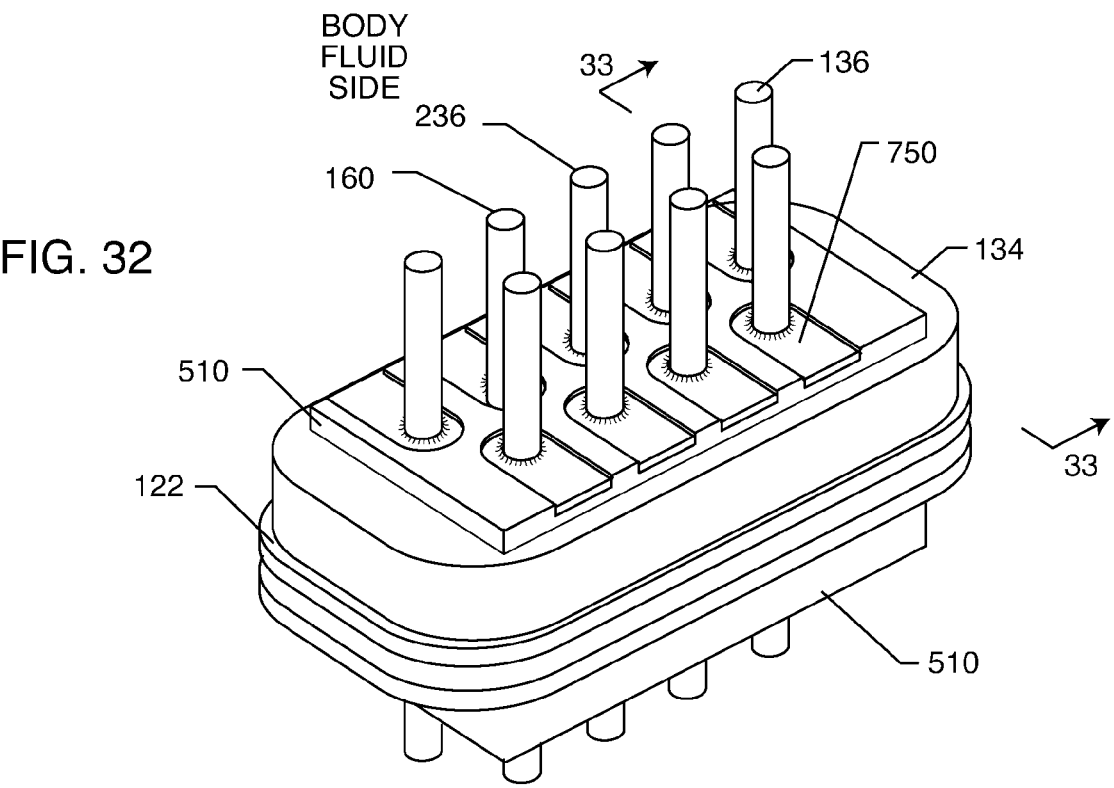
FIG. 32 is a perspective view of the assembled 9-pole filter feedthrough capacitor hermetic terminal of FIG. 31.

FIG. 31 illustrates an exploded view of an internally grounded dual inline 9-pole filtered feedthrough capacitor 510 hermetic terminal of the present invention. In the exploded view, one can see the wire bond pads 750, which are typically of gold plated Kovar or the like, on both the body fluid side as well as the side to be disposed within the active medical implant device. The alumina substrate 740 has convenient recesses and metallized areas 164 (typically of gold or nickel coated tungsten) suitable for metallurgical connection via gold brazing material or preforms 168 to the wire bond pads 750. An adhesive coated polyimide nonconductive preform 228 bonds the alumina substrate 740 to the ceramic feedthrough capacitor 510. As previously mentioned, internally grounded feedthrough capacitors are well known in the art. As described in U.S. Pat. No. 5,905,627, it is preferable that the ground pin 236 be centered to provide a low inductance path to the feedthrough capacitor active electrode plates (not shown). Accordingly, ground pin 236 has been centrally located and solidly welded, gold brazed or machined into the metallic ferrule 122, as illustrated in FIG. 32. All of the other pins 136 are in nonconductive relationship with the ferrule 122 as previously described in the prior art.

FIG. 32 illustrates a perspective view of the completed assembly of FIG. 31. As one can see, convenient wire bond attachment can be made to the wire bond pads 750. It should also be noted that there are a number of alternative shapes including L-shapes that could be used for these wire bond pads.

Figure 33:
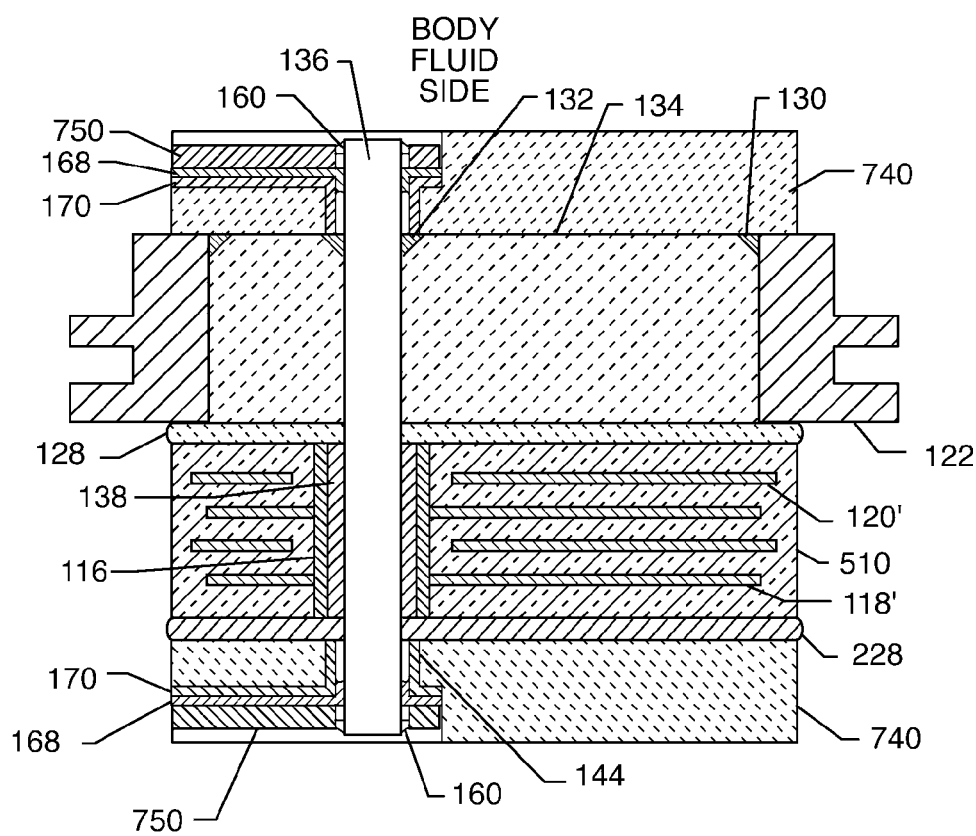
FIG. 33 is an enlarged cross-sectional view taken generally along the line 33-33 of FIG. 32.

FIG. 32 is a cross-sectional view of the 9-pole internally grounded feedthrough capacitor of FIG. 32. As one can see in the cross-sectional view, laser weld connection 160 is made between each wire bond pad 750 and the corresponding terminal pin 136. In a particularly preferred embodiment, as illustrated and described above, the wire bonding pads 750 are conductively coupled, such as by weld 160, to opposite ends of the terminal pins 136, as illustrated in FIG. 33. This enables lead wires to be connected both internally and externally of the active implantable medical device housing and be conductively coupled to the terminal pin 136, which is hermetically sealed and yet provides electric conductivity through the hermetic assembly. Moreover, as is the case in FIG. 33, feedthrough capacitors 510 can be utilized to remove potentially damaging EMI.

Figure 34:
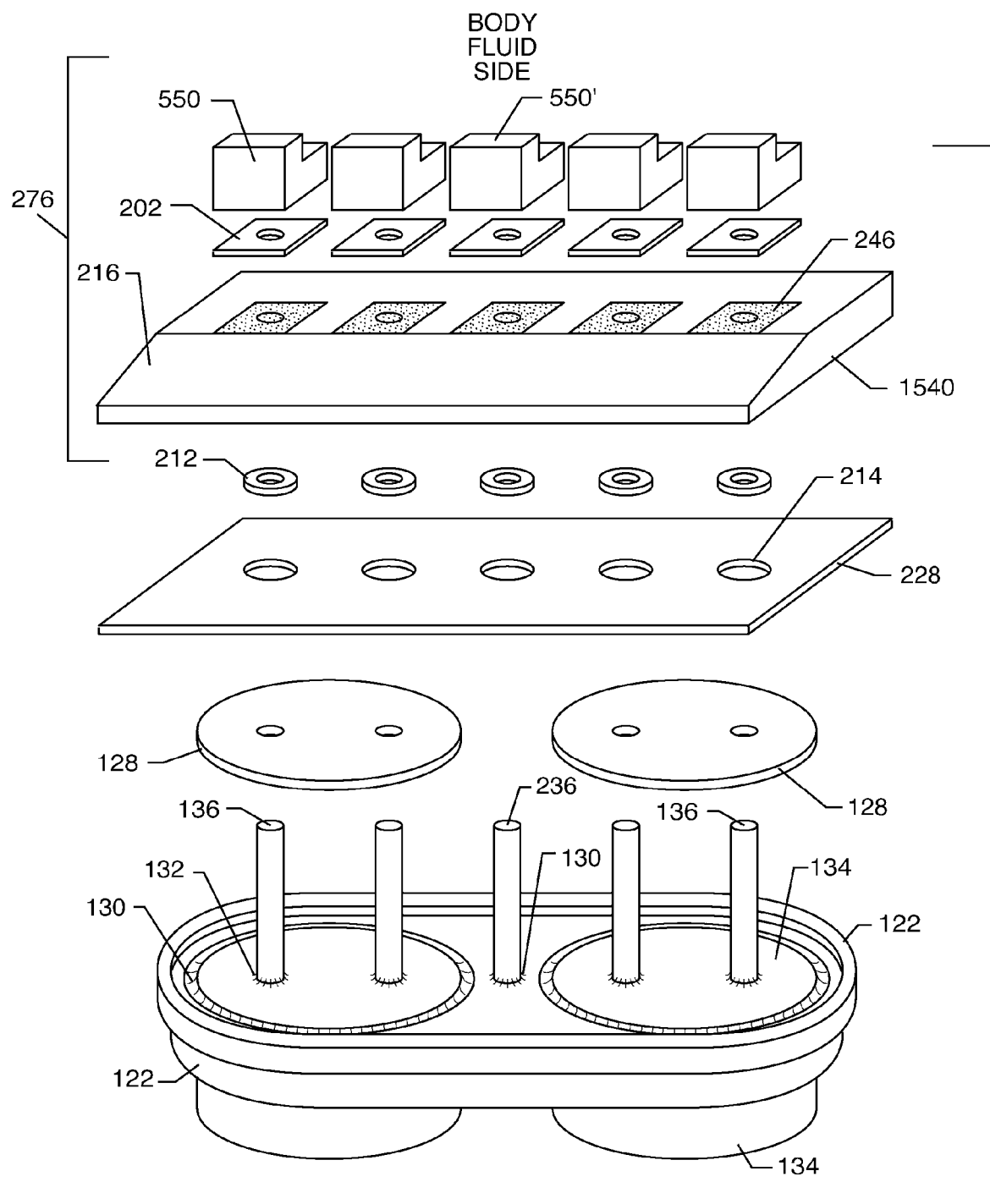
FIG. 34 is an exploded perspective view of an internally grounded quadpolar feedthrough capacitor embodying the present invention.

FIG. 34 illustrates an exploded view of an internally grounded quadpolar plus ground pin hermetic terminal for human implant applications. The internally grounded feedthrough assembly has four active feedthrough pins 136 and one ground pin 236. The ground pin 236 is shown welded to ferrule 122 in the center which is desirable, such as for use as a convenient ground point. This is because terminal pin 236 is brazed or welded directly to the ferrule 122 of the assembly. In many cases, a ground to the titanium housing 124 is required. By providing a grounded wire bond pad 550', as illustrated in FIGS. 34-36, this avoids the need to provide a special grounding location on the titanium housing of the implantable medical device.

One can see that alumina substrate 1540 of the present invention has rectangular metallized areas 246 for convenient attachment of wire bond pads 550 and 550' to these metallized areas using braze preforms 202. The wire bond pads 550 and 550' would typically be attached to substrate 1540 as a first step by reflowing the braze preforms 202 in a high temperature vacuum brazing furnace. The next step would be to assemble hermetic seal 122, 134 using a sandwich construction by first inserting the two nonconductive adhesive coated polyimide preforms 128 over the terminal pins 136 and seating them against each of the alumina insulators 134. Adhesive coated nonconductive polyimide insulating washer 228 would then be put in place and the solder or thermosetting conductive preforms 212 would be loaded so that they seat inside the through holes 214 of insulating washer 228. The pre-assembly 276 consisting of the substrate 1540 with the gold braze wire bond pad 550 would then be slipped in place over the five lead wires 136. Metallization 246 on the bottom of the substrate 1540 (not shown) is designed to press up against the five solder or thermosetting conductive adhesive preforms 212. Electrical connection is made from this bottom metallization of substrate 1540 up through each one of its metallized via holes so that there is a continuous electrical connection to the top surface metallization 246. Because of the gold braze 202 attachment of the wire bond pads 550 and 550', this means that there will be a continuous electrical circuit from wire bond pads 550 and 550' through to the terminal pins 136 and 236. This sandwich as shown exploded in FIG. 34 is then clamped together and cured at a high temperature such that the nonconductive bonding washers 228 and 128 are cured and that the solder preforms or thermosetting conductive polyimide preforms 212 are either reflowed or cured as well.

Figure 35:
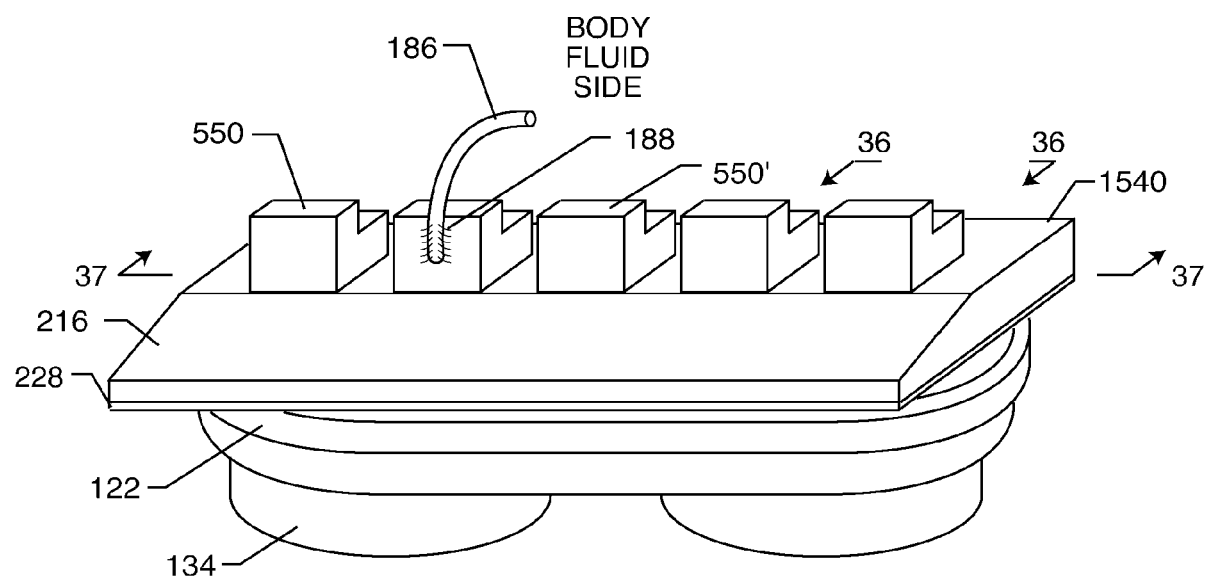
FIG. 35 is a perspective view of the assembled feedthrough terminal assembly of FIG. 34.
Figure 36:
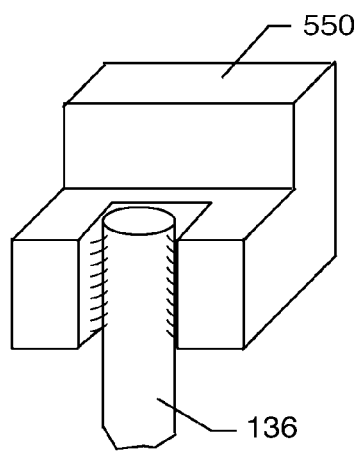
FIG. 36 is a cross-sectional view taken generally along the line 36-36 of FIG. 35.

FIG. 35 illustrates the completed assembly of FIG. 34. For illustrative purposes a lead wire 186 is shown wire bonded 188 to one of the wire bond pads 550. Wire bonding equipment, including automated systems with robotic controls typically have a rather large feed head through which the wire to be bonded protrudes. The wire bond equipment feed head tapers to a point and is somewhat conical in cross-section. Accordingly, substrate 1540 has been tapered down into area 216 thereby providing sufficient space for the wire bond head to come in and properly engage the leads 186 and wire bond pads 550. This is a novel aspect of the present invention that can be adapted to many other of the substrates that are described in this patent application. The center wire bond pad 550' is grounded to ferrule 122 of the hermetic terminal.

Referring now back to FIG. 34, one can see by observing pin 236 and gold braze or weld 130 that terminal pin 236 is both mechanically and electrically connected to the center of overall metallic ferrule structure 122.

Wire bond pad 550' is not necessary in all implantable medical devices. In certain cardiac pacemakers and implantable defibrillators, a convenient grounding location is an important feature. For example, in an implantable defibrillator cardioverter, where the titanium housing of the device can also be a cardiac shock electrode, a low resistance connection must be made from the high voltage output circuitry of the implantable defibrillator to its overall titanium housing 124. Accordingly, wire bond pad 550' provides a convenient place to make such a connection. The rest of this shock electrode circuit is completed by laser welding the ferrule 122 into the overall housing or titanium shield 124 of the implantable medical device (not shown).

FIG. 36 illustrates a cross-sectional view of the quadpolar plus ground pin assembly of FIG. 35. Referring to FIG. 36, one can see that the wire bond pads 550 have been attached by brazing material 202 to the top metallization 146 of the alumina substrate 1540. A laser weld connection 160 is made between terminal pin 136 and the wire bond pad 550 or 550'.

Wire bond pads 1150 can be placed on the other side of the hermetic terminal assembly and are brazed 230 directly to the alumina insulator 134. Human body fluid is very corrosive. Accordingly, the wire bond pads 550 or 1150, the braze 230 and the underlying lead material 136 must be of suitable biocompatible material. Such materials include the group of platinum, niobium, gold, tantalum, titanium, stainless and their various alloys including alloys containing iridium and nickel.

Attachment of lead wires 186 (not shown) to the body fluid side wire bond pads is preferably done by direct lead wire welding or brazing. These lead wires would typically connect from the wire bond pads 1150 to the connector or header block (not shown) of a cardiac pacemaker and the like. If attachment to wire bond pads 1150 is by mechanical attachment, ultrasonic bonding or thermosonic bonding, then wire bond pads 1150 would either be of gold or would require an ultra-pure gold over plating.

Figure 37:
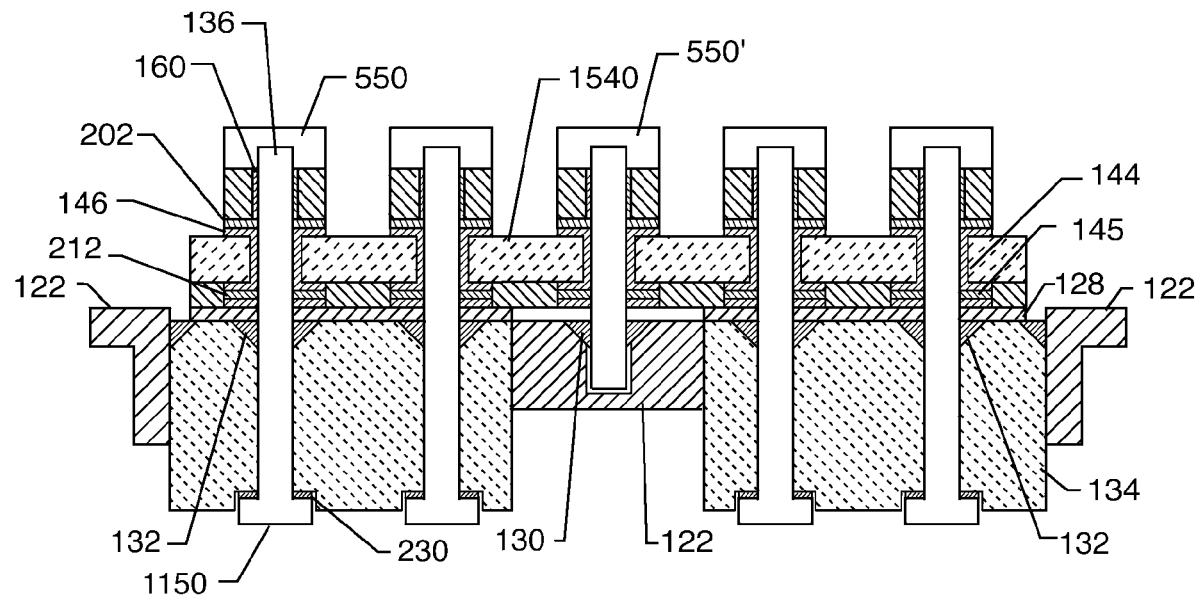
FIG. 37 is a perspective view of modified L-shaped wire bond pad taken generally of the structure illustrated by the line 37-37 in FIG. 35.

FIG. 37 illustrates a rotated close up view of one of the wire bond pads 550 of FIG. 35. As one can see, the laser weld area 160 is relatively long about both sides of the terminal pin 136. This not only makes a highly reliable electrical connection, but is also easy to manufacture. This is because there is a natural fillet area that is formed between the outside diameter of terminal pin 136, and the inside of the slot 222 which has been conveniently machined or stamped into the wire bond pad 550. As previously mentioned, it would be typical that wire bond pad 550 be of Kovar, Alloy 42, or other metallic material. Wire bond pad 550 would typically be first nickel plated and over plated with an ultra pure soft gold.

Figure 38:
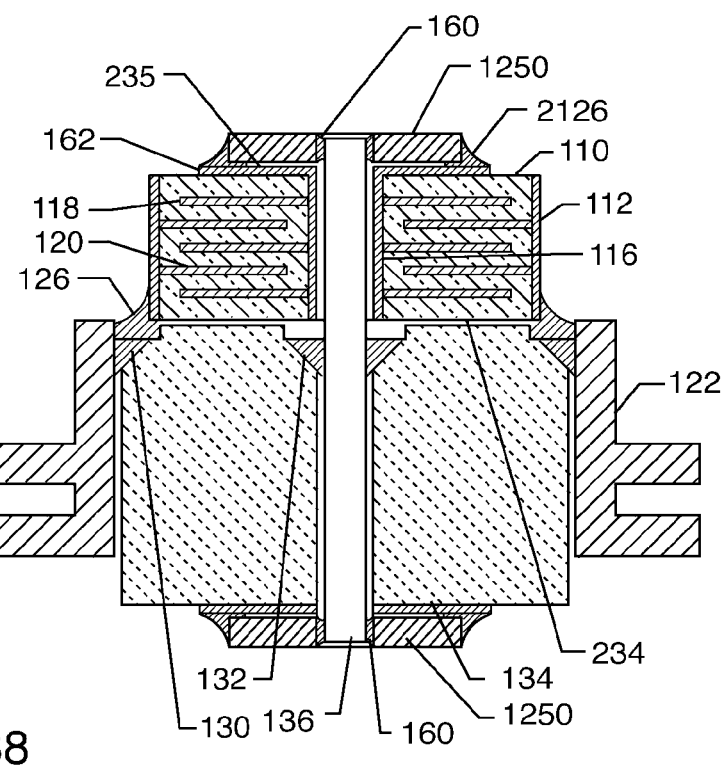
FIG. 38 is a cross-sectional view of another unipolar hermetic terminal embodying the invention.

FIG. 38 illustrates another embodiment of the present invention. Shown is a unipolar hermetic terminal with a unipolar feedthrough capacitor 110 shown attached. The novel aspect shown in FIG. 38 is that there are no nonconductive insulating washers that have been described in previous figures. The unipolar feedthrough capacitor 110 as illustrated in FIG. 38 is very simple to manufacture. A unique feature is the pedestal area which is the protruding part of the alumina insulator 134 labeled as 234. Alumina ceramic insulators can be machined, made of pressed powders and then fired, or laser cut. Accordingly, forming of the pedestal area 234 is a relatively easy and inexpensive manufacturing operation. As previously described, laser welds 130 and 132 make a mechanical and hermetic seal connection between alumina insulator 134 and both the ferrule 122 and terminal pin 136. Manufacturing of the unipolar EMI filter capacitor assembly as shown in FIG. 38 is relatively simple. All that is involved is to drop capacitor 110 over terminal pin 136 and then also place wire bond cap 1250 on top of capacitor 110. Fixturing would then apply pressure to center and push down on wire bond pad 1250 while automated equipment formed the laser weld 160 as shown. At this point the ceramic capacitor is captured between the pedestal area 234 of the alumina insulator 134 and the wire bond pad 1250. It is then easy to either manually or robotically dispense a thermosetting conductive polymer 2126 and 126 both around the outside diameter of the Kovar pad 1250 and the capacitor outside diameter termination 112 as shown. The connection material 2126 makes electrical contact between the wire bond pad 1250 and the top metallization ring 162 of the ceramic capacitor 110. The top metallization ring 162 forms a continuous electrical connection to the capacitor inside diameter metallization 116 and to the active electrodes 118 of the feedthrough capacitor 110. A wire bond pad 1250 on the body fluid side can be welded to the terminal pin 136 and attached to the alumina insulator 134 in the same manner.

Referring now to the outside diameter of feedthrough capacitor 110, electrical connection material 126 makes an electrical contact between the outside diameter termination 112 of the feedthrough capacitor 110 and the gold braze area 130 of the hermetic terminal ferrule 122. The outside diameter metallization 112 of the capacitor 110 is electrically connected to its ground electrode plates 120. Co-pending U.S. patent application Ser. No. 10/377,086 describes the importance of making electrical contact to a gold surface instead of directly to the titanium ferrule 122. This is because titanium is notorious for forming oxides which could preclude the proper performance of the EMI filter at high frequency.

An alternative method of assembling the unipolar capacitor 110 shown in FIG. 38 would be to first pre-assemble the wire bond cap 1250 to the ceramic capacitor 110 by making the mechanical and electrical connection 2126 to the top metallization 162 of the feedthrough capacitor 110. In this way the capacitor and Kovar pad assembly could be tested and then stored in inventory. When it came time to attach this pre-assembly to the hermetic terminal, all that would need to be done is to mount the assembly in place and perform the laser weld 160 to terminal pins and make the electrical connection 126 ground the capacitor outside diameter termination 112 as previously described.

As mentioned, the assembly of FIG. 38 does not incorporate the nonconductive bonding washers 228 used in previously described embodiments. This results in a space or air gap 235 between the wire bond cap 1250 and the capacitor 110. This gap is very small but could present a concern where contaminants could be trapped. Accordingly, the assembly of FIG. 38 is best suited for low voltage pacemaker applications.

Again referring to FIG. 38, one can see that a disadvantage of the wire bond cap 1250 shown is that it has a central through hole where the laser weld connection 160 is made to lead wire 136. This reduces the top surface contact area of the wire bond pad 1250 that is available for subsequent wire bonding to the lead wires.

Figure 39:
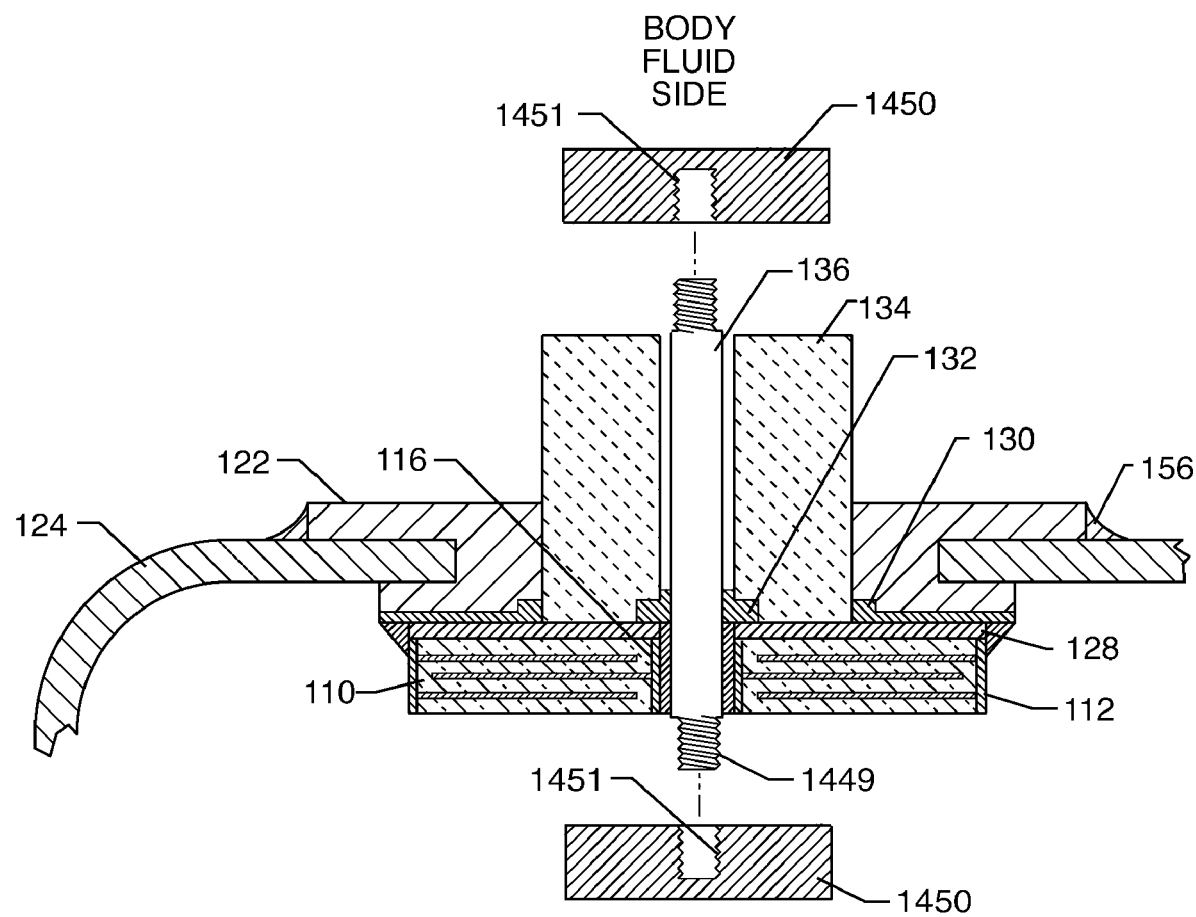
FIG. 39 is a sectional view of yet another embodiment of the invention similar to that shown in FIG. 6, wherein the wire bond cap has been drilled and threaded.

In FIG. 39, an alternative method of attaching wire bond cap 1450 is illustrated. FIG. 39 is similar to FIG. 6. The novel wire bond cap 1450 has been drilled and threaded 1451 as shown. This is designed to mate up with a threaded portion 1449 of terminal pin 136. Such threads can typically be formed using screw machines and the like. In a particularly preferred embodiment, as illustrated, opposite ends of the terminal pin 136 include external threads such that a wire bond cap 1450 can be threadedly inserted onto the ends for attachment to lead wires either extending from the internal circuitry within the housing 124 of the device, or externally on the body fluid side of the device. The threaded-on wire bond cap 1450 is typically constructed of Kovar or Alloy 42 which is then nickel plated and then over plated with pure gold suitable for wire bonding. The shape of the wire bond cap of 1450 can be circular, rectangular, hexagonal or any other shape to fit a convenient tool for screwing the device into place. Additionally, a bonding washer (not shown) could be used sandwiched between the threaded wire bond cap 1450 and the top surface of the ceramic capacitor 110. After threading the wire bond cap 1450 into place, this washer could be cured which would firmly seat the threaded cap into position so that it would be able to withstand shock and vibration forces. Of course, there are a number of other methods of securing the threaded portion 1450 and 1499 using resistance welding, laser welding, solders, thermal setting conductive adhesives on the threads and the like. Additionally, many of the wire bond embodiments shown throughout the Figures in this application could be adapted to threading as illustrated in FIG. 39.

Although several embodiments of the present invention have been described in detail for purposes of illustration, various modifications of each may be made without departing from the spirit and scope of the invention. Accordingly, the invention is not to be limited, except as by the appended claims.

What is claimed is:

1. A feedthrough terminal assembly for an active implantable medical device, comprising:
   a conductive terminal pin extending through a housing for the active implantable medical device in non-conductive relation;
   a non-conductive insulator disposed between the terminal pin and the housing; and
   a wire bond pad conductively coupled to a portion of the terminal pin on a body fluid side of the assembly, the wire bond pad adapted to have a lead wire conductively attached thereto.

2. The assembly of claim 1, wherein the wire bond pad is comprised of or coated with a conductive and biocompatible material.

3. The assembly of claim 2, wherein the wire bond pad is comprised of or coated with a noble metal, titanium or stainless steel.

4. The assembly of claim 1, wherein the wire bond pad is attached to the insulator and the terminal pin.

5. The assembly of claim 4, wherein a high temperature thermal setting material attaches the insulator and the wire bond pad.

6. The assembly of claim 1, including a second wire bond pad conductively attached to a portion of the terminal pin within the housing of the active implantable medical device.

7. The assembly of claim 6, wherein either or both of the wire bond pads are comprised of Kovar or Alloy 42.

8. The assembly of claim 1, wherein the wire bond pad is disposed over an end of the terminal pin.

9. The assembly of claim 8, wherein the wire bond pad includes a socket for receiving an end of the terminal pin therein.

10. The assembly of claim 9, wherein the wire bond pad is resistance welded to the terminal pin.

11. The assembly of claim 1, wherein the wire bond pad is mechanically attached to the terminal pin.

12. The assembly of claim 11, wherein the wire bond pad is threaded onto an end of the terminal pin.

13. The assembly of claim 1, wherein the wire bond pad includes an aperture, hole or slot for facilitating laser welding of the wire bond pad to the terminal pin.

14. The assembly of claim 1, wherein the wire bond pad is spaced apart from the insulator and supported solely on the terminal pin.

15. The assembly of claim 1, wherein the wire bond pad includes an extension to which the lead wire is attached.

16. The assembly of claim 15, wherein first and second portions of the wire bond pad are angularly displaced relative to one another.

17. The assembly of claim 1, wherein the wire bond pad includes an aperture through which the terminal pin extends.

18. The assembly of claim 1, including a non-conductive substrate having an aperture into which the terminal pin extends.

19. The assembly of claim 18, wherein the substrate includes a conductive surface trace having a bonding area.

20. The assembly of claim 19, wherein the wire bond pad is conductively attached to the bonding area.

21. The assembly of claim 20, wherein the substrate aperture is substantially lined with a conductive material conductively coupled to the surface trace and bonding area.

22. The assembly of claim 18, wherein the substrate includes a tapered edge and comprises multiple apertures therethrough for passage of multiple terminal pins, including a ground pin, and wherein wire bond pads are conductively coupled to each terminal pin.

23. The assembly of claim 18, wherein the substrate is selected from an alumina, ceramic, berrylia, aluminum nitride, Fosterite, polyimide, cyanate ester, barium titanate, epoxy or fiber-reinforced material.

24. The assembly of claim 1, including a conductive ferrule conductively coupled to the housing of the active implantable medical device, through which the terminal pin extends in non-conductive relation.

25. The assembly of claim 1, wherein the substrate comprises a ceramic-based material.

26. The assembly of claim 1, further comprising:
   a conductive ferrule adapted to be conductively coupled to the housing of the active implantable medical device wherein the conductive terminal pin extends through the ferrule in non-conductive relation and wherein the non-conductive insulator is disposed between the terminal pin and the ferrule; and
   a feedthrough capacitor having an aperture for the terminal pin to extend therethrough, the capacitor including a first set of electrode plates conductively coupled to the terminal pin, and a second set of electrode plates conductively coupled to the ferrule.

27. The assembly of claim 26, wherein the wire bond pad is comprised of or coated with a conductive and biocompatible material.

28. The assembly of claim 27, wherein the wire bond pad is comprised of or coated with a noble metal, titanium or stainless steel.

29. The assembly of claim 26, wherein the wire bond pad is attached to the insulator and the terminal pin.

30. The assembly of claim 29, wherein a high temperature thermal setting material attaches the insulator and the wire bond pad.

31. The assembly of claim 26, including a second wire bond pad conductively attached to a portion of the terminal pin within the housing of the active implantable medical device.

32. The assembly of claim 31, wherein either or both of the wire bond pads are comprised of Kovar or Alloy 42.

33. The assembly of claim 31, wherein the second wire bond pad is disposed adjacent to the capacitor and conductively coupled to the terminal pin.

34. The assembly of claim 33, including an electrically insulative material disposed between the wire bond pad and the capacitor.

35. The assembly of claim 31, wherein the second wire bond pad is conductively coupled to the first set of electrode plates.

36. The assembly of claim 31, including a substrate disposed adjacent to a planar surface of the capacitor and configured to at least partially protect the capacitor from forces incident to conductive coupling of the lead wire to the first set of electrode plates.

37. The assembly of claim 36, wherein the wire bond pad is attached to the substrate.

38. The assembly of claim 36, including a conductive insert ring disposed within a recess in the substrate, the insert ring being conductively coupled to the terminal pin and the substrate.

39. The assembly of claim 38, wherein the substrate includes a conductive trace conductively coupled to the insert ring, and defining a bonding area on a surface of the substrate.

40. The assembly of claim 39, wherein the second wire bond pad is conductively attached to the bonding surface.

41. The assembly of claim 26, wherein the wire bond pad is disposed over an end of the terminal pin.

42. The assembly of claim 41, wherein the wire bond pad includes a socket for receiving an end of the terminal pin therein.

43. The assembly of claim 42, wherein the wire bond pad is resistance welded to the terminal pin.

44. The assembly of claim 26, wherein the wire bond pad is mechanically attached to the terminal pin.

45. The assembly of claim 44, wherein the wire bond pad is threaded onto an end of the terminal pin.

46. The assembly of claim 26, wherein the wire bond pad includes an aperture, hole or slot for facilitating laser welding of the wire bond pad to the terminal pin.

47. The assembly of claim 26, wherein the wire bond pad is spaced apart from the insulator and supported solely on the terminal pin.

48. The assembly of claim 26, wherein the wire bond pad includes an extension to which the lead wire is attached.

49. The assembly of claim 48, wherein first and second portions of the wire bond pad are angularly displaced relative to one another.

50. The assembly of claim 26, wherein the wire bond pad includes an aperture through which the terminal pin extends.

51. The assembly of claim 26, including a non-conductive substrate having an aperture into which the terminal pin extends.

52. The assembly of claim 51, wherein the substrate includes a conductive surface trace having a bonding area.

53. The assembly of claim 52, wherein the wire bond pad is conductively attached to the bonding area.

54. The assembly of claim 53, wherein the substrate aperture is substantially lined with a conductive material conductively coupled to the surface trace and bonding area.

55. The assembly of claim 51, wherein the substrate includes a tapered edge.

56. The assembly of claim 55, wherein the substrate includes multiple apertures therethrough for passage of multiple terminal pins, including a ground pin, and wherein wire bond pads are conductively coupled to each terminal pin.

57. The assembly of claim 51, wherein the substrate comprises a ceramic-based material.

58. The assembly of claim 51, wherein the substrate is selected from an alumina, ceramic, berrylia, aluminum nitride, Fosterite, polyimide, cyanate ester, barium titanate, epoxy or fiber-reinforced material.

* * * * *